United States Patent
Ma et al.

(10) Patent No.: US 10,975,128 B2
(45) Date of Patent: Apr. 13, 2021

(54) **RECOMBINANT *DERMATOPHAGOIDES FARINAE* TYPE 1 ALLERGEN PROTEIN AND ITS PREPARATION METHOD AND APPLICATION**

(71) Applicant: ZonHon Biopharma Institute, Inc., Jiangsu (CN)

(72) Inventors: Bruce Yong Ma, Jiangsu (CN); Yu Fan, Jiangsu (CN); Jun Wang, Jiangsu (CN); Anliang Wang, Jiangsu (CN)

(73) Assignee: ZonHon Biopharma Institute, Inc., Jiangsu (CN)

( * ) Notice: Subject to any disclaimer, the term of this patent is extended or adjusted under 35 U.S.C. 154(b) by 0 days.

(21) Appl. No.: 16/456,357

(22) Filed: Jun. 28, 2019

(65) Prior Publication Data

US 2019/0389919 A1  Dec. 26, 2019

Related U.S. Application Data

(63) Continuation of application No. PCT/CN2017/119190, filed on Dec. 28, 2017.

(30) Foreign Application Priority Data

Dec. 31, 2016 (CN) .......................... 201611267250.7

(51) Int. Cl.
*C07K 14/435* (2006.01)
*A61K 38/00* (2006.01)

(52) U.S. Cl.
CPC ........ *C07K 14/43531* (2013.01); *A61K 38/00* (2013.01)

(58) Field of Classification Search
None
See application file for complete search history.

(56) References Cited

FOREIGN PATENT DOCUMENTS

CN     1780852 A       5/2006
WO     2001/29078 A2   4/2001

OTHER PUBLICATIONS

GenBank Accession No. BAC53948, Der f 1 allergen preproenzyme [Dermatophagoides farinae]. 3 pages, May 23, 2017.
Lu, Research progress on the expression system and secretory protein of Pasteur Pichia pastoris. Journal of Clinical and Experimental Medicine. Mar. 2004;3(1):43-47.
Takai et al., Analysis of the structure and allergenicity of recombinant pro- and mature Der p 1 and Der f 1: major conformational IgE epitopes blocked by prodomains. J Allergy Clin Immunol. 2005;115(3):555-563.
Takai et al., Modulation of allergenicity of major house dust mite allergens Der f 1 and Der p 1 by interaction with an endogenous ligand. J Immunol. 2009;183(12):7958-7965.
Takai et al., Recombinant Der p 1 and Der f 1 with in vitro enzymatic activity to cleave human CD23, CD25 and alpha1-antitrypsin, and in vivo IgE-eliciting activity in mice. Int Arch Allergy Immunol. 2005;137(3):194-200.
Yasuhara et al., Cloning and expression of cDNA encoding the complete prepro-form of an isoform of Der f 1, the major group 1 allergen from house dust mite Dermatophagoides farinae. Biosci Biotechnol Biochem. 2001;65(3):563-569.
Zhao et al., Synonymous Codon Usage in Pichia pastoris. Chinese Journal of Biotechnology. May 2000;16(3):308-311.
International Search Report for Application No. PCT/CN2017/119190, dated Mar. 23, 2018, 15 pages.

*Primary Examiner* — Padmavathi Baskar
(74) *Attorney, Agent, or Firm* — McCarter & English, LLP

(57) ABSTRACT

Provided are an optimized proDer f1 gene, a proDer f1 protein encoded thereby, a vector comprising said gene, and a *Pichia pastoris* strain. Also provided are an expression method and a purification method of the proDer f1 protein.

4 Claims, 15 Drawing Sheets

Specification includes a Sequence Listing.

Sequence before optimization
Sequence after optimization

```
  1 CGTCCAGCTTCAATCAAAACTTTTGAAGAATTCAAAAAAGCCTTCAACAAAAACTATGCC
    |  |||||  || ||||||  ||  ||||||||| |||||  |||||  || |||||  |||||  |||
  1 AGACCAGCATCTATCAAGACATTTGAAGAGTTCAAGAAAGCTTTTAACAAGAACTACGCC

61 ACCGTTGAAGAGGAAGAAGTTGCCCGTAAAAACTTTTTGGAATCATTGAAATATGTTGAA
    || |||||||||||||| || ||  | || |||||||||||||| ||||| ||||||||
 61 ACTGTTGAAGAGGAAGAGGTCGCTAGAAAGAACTTTTTGGAATCTTTGAAGTATGTTGAG

121 GCTAACAAAGGTGCCATCAACCATTTGTCCGATTTGTCATTGGATGAATTCAAAAACCGT
    || ||||||||||| || || || |||||  |||||||||| | ||  |||||||| ||  |
121 GCAAACAAAGGTGCTATTAATCACTTGTCTGATTTGTCCCTTGACGAATTCAAGAACAGA

181 TATTTGATGAGTGCTGAAGCTTTTGAACAACTCAAAACTCAATTCGATTTGAATGCCGAA
    || ||||||||||||||||| ||||| ||| || |||||  | || ||||||
181 TACTTGATGAGTGCTGAAGCCTTTGAGCAATTGAAAACACAGTTCGACCTTAACGCCGAA

241 ACAAGCGCTTGCCGTATCAATTCGGTTAACGTTCCATCGGAATTGGATTTACGATCACTG
    ||  || || | |||| |||  ||| ||  || || ||| ||   ||
241 ACCTCAGCATGTAGAATTAACTCAGTTAATGTCCCTAGTGAGTTGGATCTTAGAAGTTTG

301 CGAACTGTCACTCCAATCCGTATGCAAGGAGGCTGTGGTTCATGTTGGGCTTTCTCTGGT
    |||| ||  ||||||| || | |||||||||| || ||||||||||  || ||||| ||
301 AGAACCGTTACTCCTATTAGAATGCAAGGTGGATGTGGTTCTTGCTGGGCCTTCTCCGGA

361 GTCGCCGCAACTGAATCAGCTTATTTGGCCTACCGTAACACGTCTTTGGATCTTTCTGAA
    || || || || ||||| |||||||  | ||| || || ||||| | | || || ||||||| ||||
361 GTTGCAGCTACCGAATCTGCTTACTTGGCCTACAGACAAACTTCATTGGATCTTAGTGAA

421 CAGGAACTCGTCGATTGCGCATCTCAACACGGATGTCACGGCGATACAATACCAAGAGGC
    || ||  | || ||  || || ||  ||  || ||  ||||| || || || || |||||
421 CAAGAGTTGGTTGACTGTGCTTCCCAGCATGGTTGCCACGGAGACACTATTCCTAGAGGT

481 ATCGAATACATCCAACAAAATGGTGTCGTTGAAGAAAGAAGCTATCCATACGTTGCACGA
    || ||||||||||||  || ||||| ||  ||| |||| |||  ||  |||||  ||
481 ATTGAATACATCCAACAGAACGGAGTTGTCGAAGAGAGATCATACCCATATGTTGCTAGA

541 GAACAACAATGCCGACGACCAAAATTCGCAACATTACGGTATCTCAAACTACTGCCAAATT
    || |||||| ||  || |||| || ||  ||||| |||||||||        ||||||||||||| ||
541 GAGCAACAGTGTAGAAGACCTAACTCAACACTACGGTATTAGTAACTACTGCCAGATC

601 TATCCACCAGATGTGAAACAAATCCGTGAAGCTTTTGACTCAAACACACACAGCTATTGCC
    ||||||||  |||||  || |||||  |  |||||||||||  || || || || || |||||||
601 TATCCACCTGATGTTAAGCAAATTAGAGAAGCATTGACACAGACCCATACTGCAATTGCT

661 GTCATTATTGGCATTAAAGATTTGAGAGCTTTTCAACATTATGATGGACGAACAATCATT
    |||||||  || || || |||||||||||||||| |||||  || || ||||||||  ||
661 GTCATTATCGGAATCAAGGATTTGAGAGCTTTCCAACATTACGACGGTAGAACAATTATC

721 CAACATGACAATGGTTATCAACCAAACTATCATGCCGTCAACATTGTCGGTTACGGAAGT
    |||| |||| ||| ||| |||| ||||||||  |||||| || || ||||| ||||||||||||
721 CAACACGATAACGGATACCAGCCAAATTATCATGCTGTTAACATTGTCGGTTACGGATCC

781 ACACAAGGCGTCGATTATTGGATCGTACGAAACAGTTGGGATACTACCTGGGGTGATAGC
    || |||||| || |||||||||| |||||| |||| |||||||||||  || || ||||||
781 ACCCAAGGTGTTGATTATTGGATCGTCAGAAACTCTTGGGATACTACATGGGGTGATTCT

841 GGATACGGATATTTCCAAGCCGGAAAACAACCTCATGATGATCGAACAATATCCATATGTT
    |||| ||||||||||||||||| |||||||||  |  |||||||||  ||||  || || |||||
841 GGTTACGGATATTTCCAAGCTGGAAACAATTTGATGATGATTGAACAGTACCCTTATGTT

901 GTAATCATGTGA
    ||  ||||||| |
901 GTCATCATGTAA
```

FIG. 1

RECOMBINANT *DERMATOPHAGOIDES FARINAE* TYPE 1 ALLERGEN PROTEIN AND ITS PREPARATION METHOD AND APPLICATION

REFERENCE TO RELATED APPLICATIONS

This application is a continuation application of International Patent Application No. PCT/CN2017/119190, filed on Dec. 28, 2017, and published as WO 2018/121639 A1, which claims priority to Chinese Patent Application No. CN201611267250.7, filed on Dec. 31, 2016. The entire contents of the above referenced applications, including the original specifications and drawings in Chinese, and any sequence listing, are hereby incorporated herein by reference.

SEQUENCE LISTING

The instant application contains a Sequence Listing which has been filed electronically in ASCII format and is hereby incorporated by reference in its entirety. Said ASCII copy, created on Aug. 5, 2019, is named 131064-00301 SL.txt and is 9,025 bytes in size.

TECHNICAL FIELD

The invention belongs to the field of bioengineering genes, and relates to a recombinant *Dermatophagoides farinae* type 1 allergen, and its coding gene and expression and purification method.

BACKGROUND OF THE INVENTION

There are many kinds of dust mites, which are widely present in human living and working environments. The excreta, metabolites and mite bodies of dust mites have strong allergenicity. According to statistics, about 10% of the world's population is allergic to dust mites, and about 80% of extrinsic asthma is caused by dust mites.

At present, a crude extract of dust mite allergens is mainly used clinically to treat allergic diseases caused by dust mites. For example, *Dermatophagoides farinae* drops, named "Changdi", of Zhejiang Wolwopharma Co., which was marketed in 2006, is an extract of metabolic culture of *Dermatophagoides farinae*. Allergens of dust mites mainly exist in excreta and mite bodies; therefore, the extraction method takes a long time with a cumbersome process and a high cost. In addition, the composition of a natural allergen extract is very complicated, it is very difficult to make its components constant, and the natural allergen extract is easy to be contaminated by exogenous toxic substances and pathogenic microorganisms. Long-term use of a crude extract of dust mite allergens can lead to local reactions such as flush, swelling, induration and necrosis; and systemic reactions such as shock, edema, bronchospasm, urticaria, angioedema and systemic erythema. In addition, in the case that the crude extract is used for diagnosis, it is impossible to specifically determine the extent of the patient's response to each component of the allergens, which may lead to misdiagnosis.

The quality of the allergen is essential for the diagnosis and treatment of allergic diseases, and the allergen used for immunodiagnosis and immunotherapy should be a pure product rather than a crude extract. Recombinant allergens have the following advantages over crude extracts: (1) the recombinant allergens have a higher purity and contain no non-allergenic components, enzymes, enzyme inhibitors and toxic proteins as compared with the crude extracts; (2) the recombinant protein has a single composition, has good specificity, while the components in the crude extract are complex, the patient may only have reactions with some of the components of the crude extract, and the specificity is poor; (3) as compared with the natural extract, the recombinant allergen reduces IgE-bound antigenic epitopes and thus reduces IgE-mediated allergic reactions effectively, at the same time the domains of allergen necessary for T cell recognition are retained to result in better immunogenicity, thereby reducing the risk of immunotherapy and improving the desensitization therapy effect.

Allergens of dust mites are complex in composition, with more than 30 types, of which type 1 and type 2 allergens are the most important allergen components. At present, the most comprehensive study on *Dermatophagoides farinae* type 1 allergen (Der f1) is a study conducted by Japanese scholar Toshiro Takai et al. in 2005. The article indicates that it is necessary to add a propeptide of Der f1 protein (Der f1 with propeptide is denoted as proDer f1) for expression of Der f1 in the *Pichia pastoris* system, otherwise Der f1 could not be expressed in an eukaryotic expression system. Then proDer f1 was activated to obtain mature Der f1 protein which is consistent with the amino acid sequence of natural protein. In this article, the proDer f1 gene was not optimized results in low yield. Currently there are no further studies reported.

SUMMARY OF THE INVENTION

In order to overcome the above-mentioned shortcomings, the inventors optimize the proDer f1 gene in the *Pichia pastoris* expression system, and add an acting element to increase the expression of proDer f1 in molecular level, and the inventors surprisingly found that proDer f1 after gene optimization is expressed at a higher level as compared with the prior art; furthermore, the activation process of proDer f1 was further studied and optimized by the inventors, in which a more operational and scalable activation process was adopted. The purified mature Der f1 protein has a similar biological activity as the natural protein.

One object of the present invention is to provide a DNA sequence encoding proDer f1 protein, having a base sequence as shown in SEQ ID NO: 1. This sequence has been codon-optimized for the *Pichia pastoris* expression system, which is more conducive to expressing proDer f1 in *Pichia pastoris*.

Another object of the present invention is to provide proDer f1 protein having an amino acid sequence as shown in SEQ ID NO: 3.

Another object of the present invention is to provide Der f1 protein having an amino acid sequence as shown in SEQ ID NO: 4.

Another object of the present invention is to provide a vector comprising the above-mentioned optimized gene encoding proDer f1, preferably, the vector is pAO815, pPIC9, pPIC9K, pPIC3.5, pPIC3.5K, pPICZαA, B, C or pGAPZαA, B, C, more preferably pPIC3.5K, pPICZαA or pGAPZαA.

Another object of the present invention is to provide a *Pichia pastoris* strain comprising the above-mentioned vector, preferably, the *Pichia pastoris* strain is SMD1168, GS115, KM71, X33 or KM71H, more preferably strain KM71 or X33.

Preferably, there is 242 bp interval between the DNA sequence encoding the proDer f1 protein and the ATG of AOX1 of *Pichia pastoris*; the DNA sequence encoding the proDer f1 protein is preceded by an alpha-factor signal peptide and Kozak sequence GCCACCATGG.

Another object of the present invention is to provide a method for expressing the proDer f1 protein, comprising the steps of:

A constructing a vector comprising the above-mentioned gene encoding proDer f1;

B linearizing the vector of step A, transferring it into a *Pichia pastoris* strain, and culturing under a suitable condition;

C recovering and purifying the protein.

The above-mentioned vector is preferably pPIC3.5K, pPICZαA or pGAPZαA.

The above-mentioned *Pichia pastoris* strain is preferably a KM71 or X33 strain.

More preferably, the above-mentioned vector is pPICZαA, and the above-mentioned *Pichia pastoris* strain is strain X33.

Another object of the present invention is to provide a method for purifying a recombinant Der f1 protein, comprising the steps of:

A centrifuging the proDer f1 fermentation broth at a low temperature and a high speed to collect a supernatant, dialyzing the supernatant in a 5 KD dialysis bag against a 25 mM sodium acetate buffer at pH 4.5 for 48 h, and filtering through a 0.45 μm filter membrane;

B the first step, cation chromatography, comprising equilibrating a chromatographic column with an equilibration buffer, passing the activated mature Der f1 fermentation broth in step A through a separation packing using a purification system, and then eluting with a gradient of an elution buffer to collect an elution peak, wherein the equilibration buffer is 50 mM sodium acetate at pH 4.5, and the elution buffer is 50 mM sodium acetate and 1.0 M sodium chloride at pH 4.5;

C the second step, comprising ultra-filtrating the Der f1 protein peak collected in step B with a 20 mM phosphate solution at pH 6.0, equilibrating a chromatographic column with an equilibration buffer, loading the ultra-filtrated Der f1 protein solution on an anion chromatography packing, and collecting a flow-through peak, wherein the equilibration buffer is 20 mM phosphate at pH 6.0; and D the third step, comprising adding ammonium sulfate to the flow-through peak in step C to the final concentration of 1.5 M, pH 6.0, equilibrating a chromatographic column with an equilibration buffer, loading a Der f1 sample on a hydrophobic chromatography packing, eluting with a gradient of an elution buffer, wherein equilibration buffer is 1.5 M ammonium sulfate and 20 mM phosphate at pH 6.0, and the elution buffer is 20 mM phosphate at pH 6.0.

Another object of the present invention is to provide the use of the recombinant Der f1 protein in the preparation of a medicament for treating a dust mite allergic disease. The allergic disease is allergic rhinitis, allergic asthma, and the like.

The recombinant Der f1 protein of the present invention has a high expression level and has similar biological activity as the natural protein.

BRIEF DESCRIPTION OF THE DRAWINGS

FIG. 1 is a comparison plot of sequences of the recombinant proDer f1 gene before and after optimization.

The sequence before optimization corresponds to the nucleotide sequence of the natural proDer f1 gene; the sequence after optimization corresponds to the nucleotide sequence of the recombinant proDer f1 gene of the present invention, that is, the codon-optimized sequence.

Figure 2A:
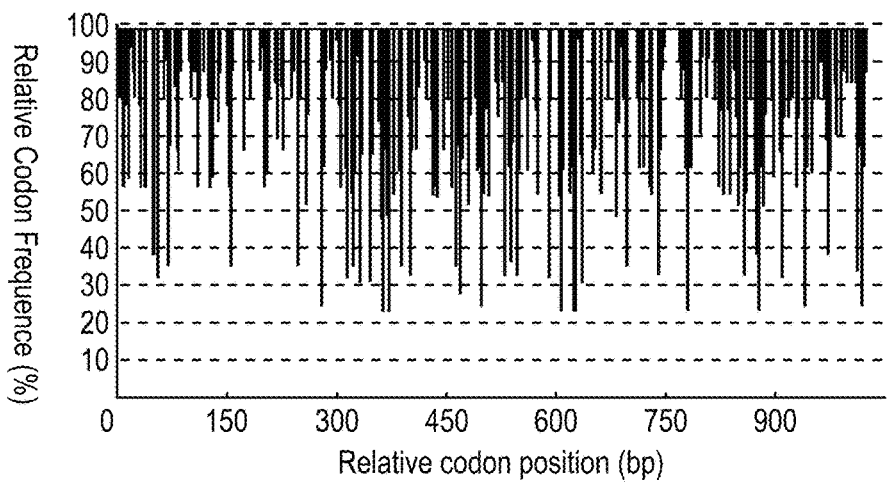
Figure 2B:
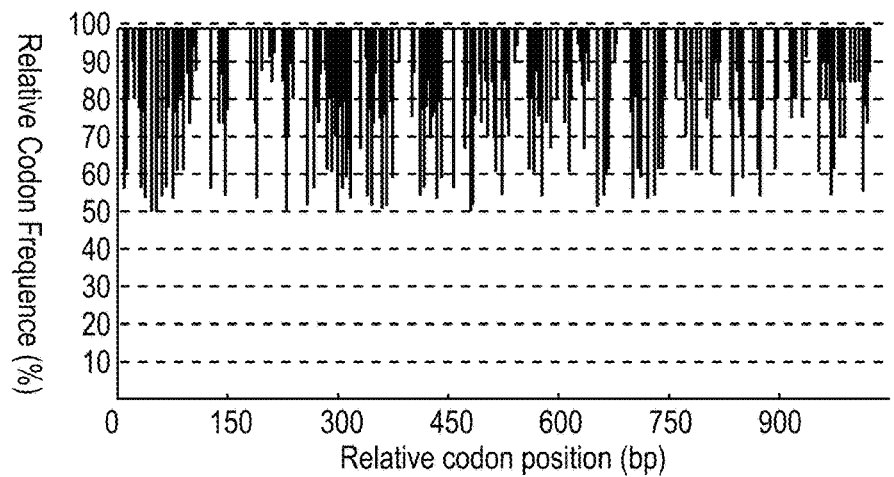

FIGS. 2A and 2B show the CAI indices of the proDer f1 gene in the *Pichia pastoris* expression system before and after optimization.

FIG. 2A shows that the CAI index of the nucleotide sequence of the natural proDer f1 gene in the *Pichia pastoris* expression system was calculated by a program to be 0.76. FIG. 2B shows that the CAI index of the optimized proDer f1 codon of the present invention in the *Pichia pastoris* expression system is calculated by a program to be 0.85.

Figure 3A:
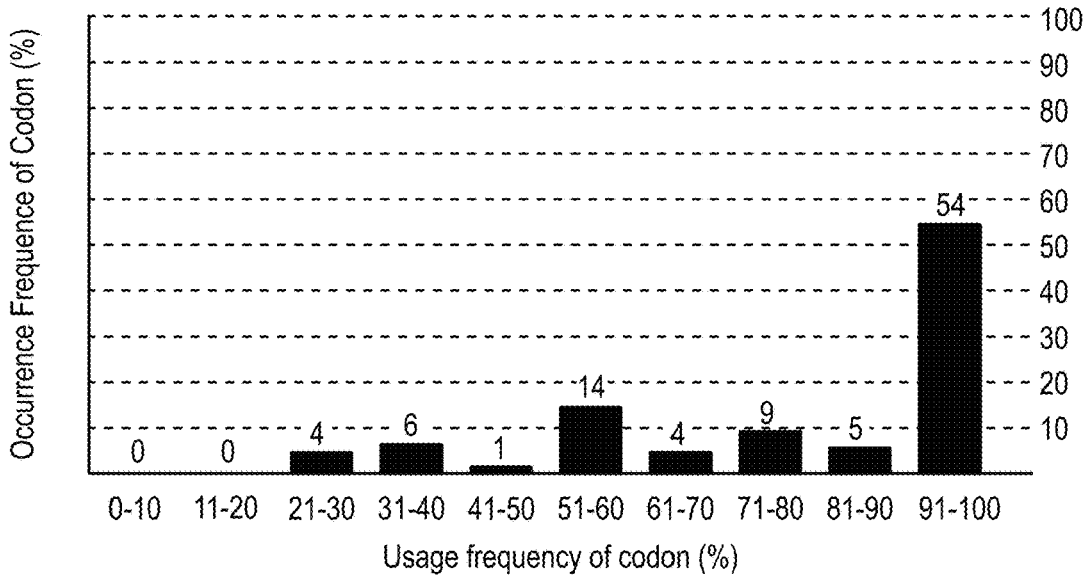
Figure 3B:
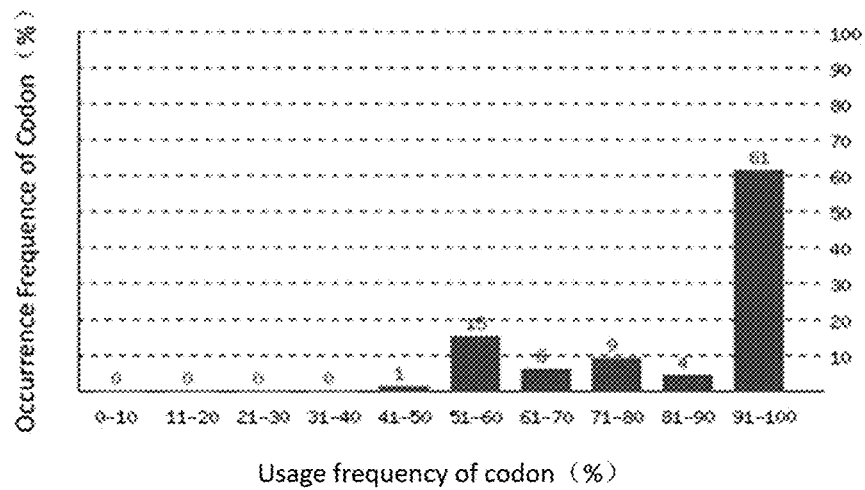

FIGS. 3A and 3B are optimal codon frequency distribution region plots of the proDer f1 gene in the *Pichia pastoris* expression host before and after codon optimization.

FIG. 3A is an optimal codon frequency distribution region plot of the nucleotide sequence of natural proDer f1 gene in the *Pichia pastoris* system, and it can be seen from the figure that the occurrence percentage of low-utilization codon in the nucleotide sequence of natural proDer f1 gene is 10%. FIG. 3B shows an optimal codon frequency distribution region plot of the optimized proDer f1 codon of the present invention in the *Pichia pastoris* system, and the occurrence rate of low-utilization codon in the sequence of optimized proDer f1 codon of the present invention is 0.

Figure 4A:
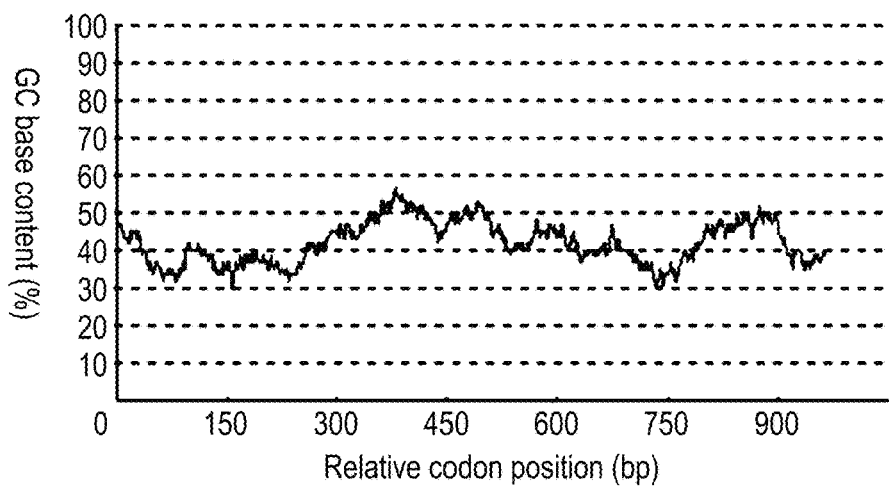
Figure 4B:
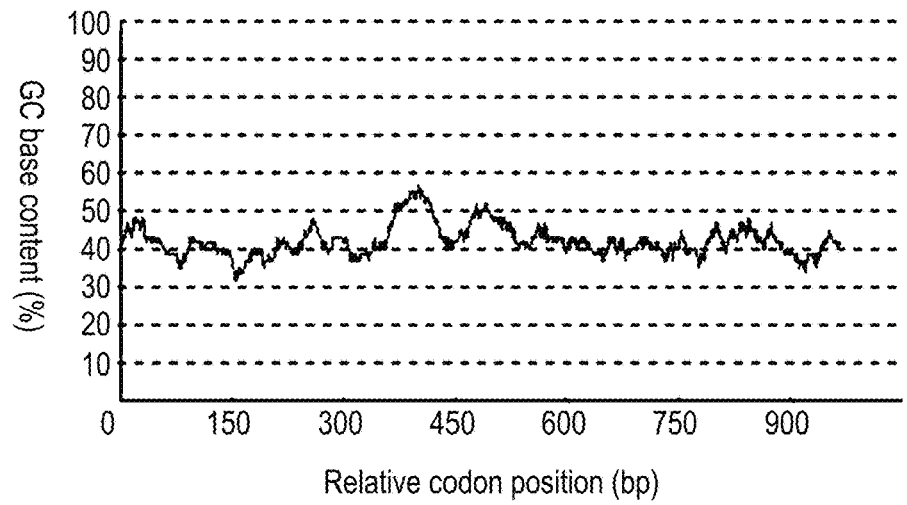

FIGS. 4A and 4B are average GC base content distribution region plots of the proDer f1 gene in the *Pichia pastoris* expression system before and after codon optimization.

FIG. 4A shows that the average GC base content of the nucleotide sequence of the natural proDer f1 gene in the *Pichia pastoris* expression system is 41.85%. FIG. 4B shows that the average GC base content of optimized proDer f1 codon of the present invention in the *Pichia pastoris* expression system is 42.10%.

Figure 5:
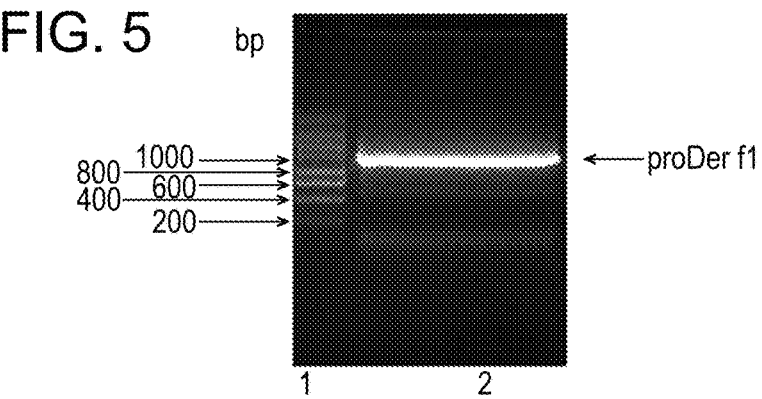

FIG. 5 is an agarose gel electrophoretogram of a PCR product of the codon-optimized proDer f1 gene.

Lane 1 represents 200 bp DNA ladder; lane 2 represents a PCR product of the recombinant proDer f1 gene containing XhoI and NotI restriction sites at both ends.

Figure 6:
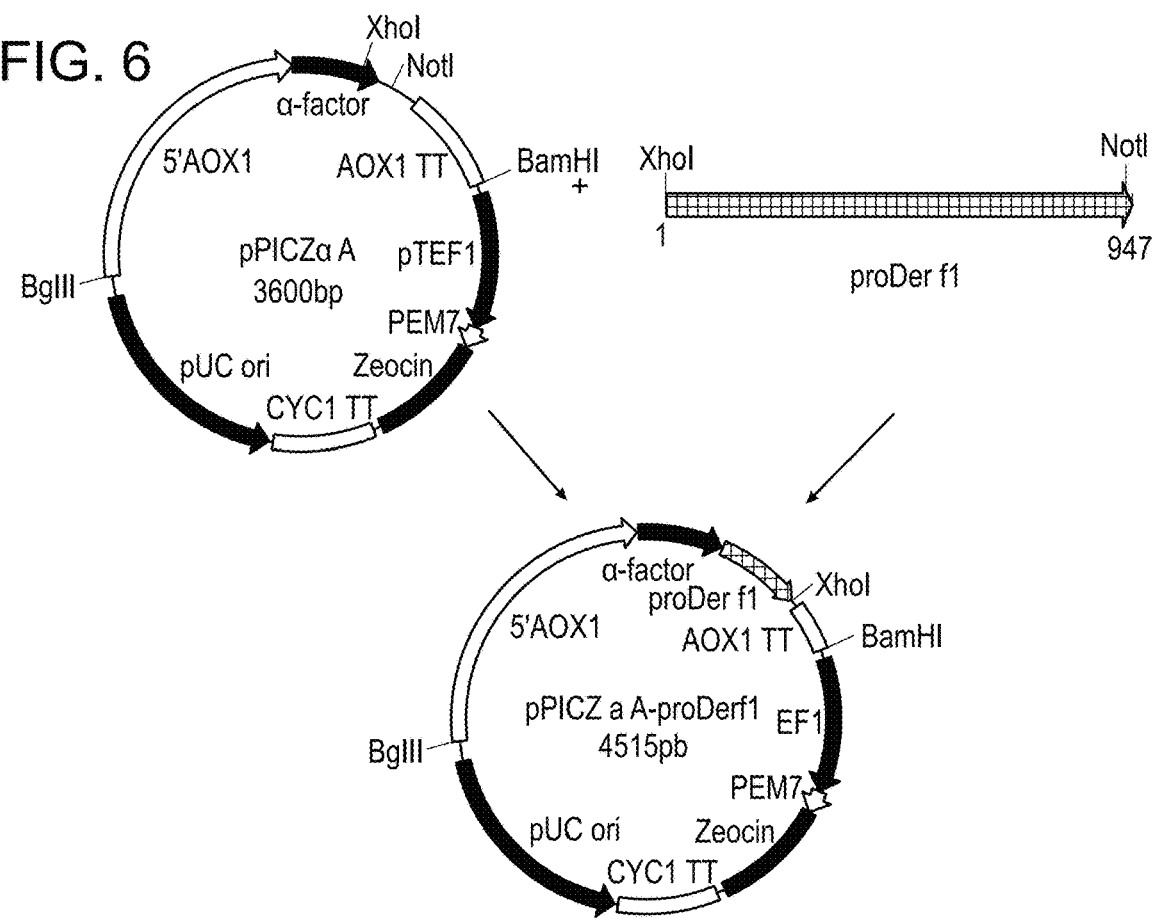

FIG. 6 is a diagram showing a construction process of the expression plasmid pPICZα-proDer f1 for codon-optimized proDer f1.

Figure 7A:
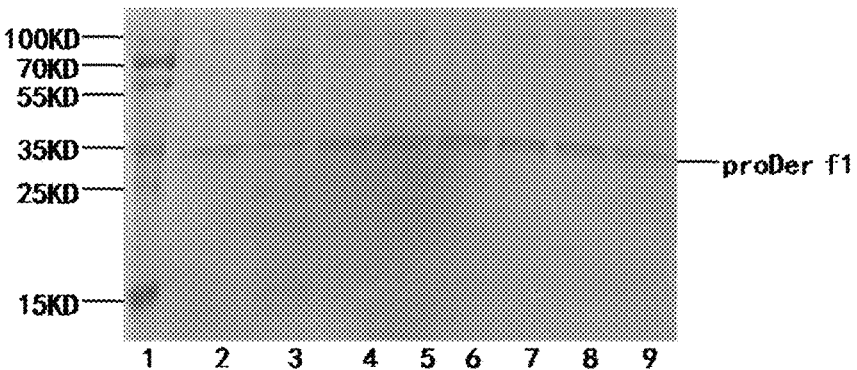
Figure 7B:
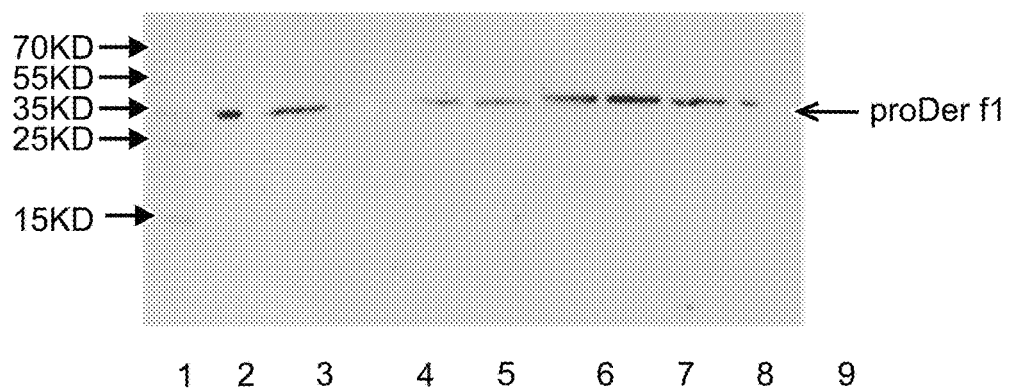

FIGS. 7A-7B are diagrams showing the identification of expression of the codon-optimized proDer f1 gene in the host engineering bacteria.

FIG. 7A is a SDS-PAGE gel electrophoretogram of a supernatant of a solution of the host engineering strain containing the codon-optimized proDer f1 gene, after methanol-induced expression for one week. Lane 1 represents pre-stained protein loading markers in the range of 10-250 KD; and other lanes represent supernatants of cultured solutions of proDer f1 gene-positive monoclonal host engineering strains screened by Zeocin.

FIG. 7B is a western blot plot of a supernatant of a solution of the host engineering strain containing the codon-optimized proDer f1 gene, after methanol-induced expression for one week. Lane 1 represents pre-stained protein loading markers in the range of 10-250 KD; and lanes 2-10 represent supernatants of proDerf1 monoclonal-induced expression FIGS. 8A-8B show a chromatogram of the supernatant of proDer f1 fermentation broth by cation chromatography of the first step, and a gel electrophoretogram.

Figure 8A:
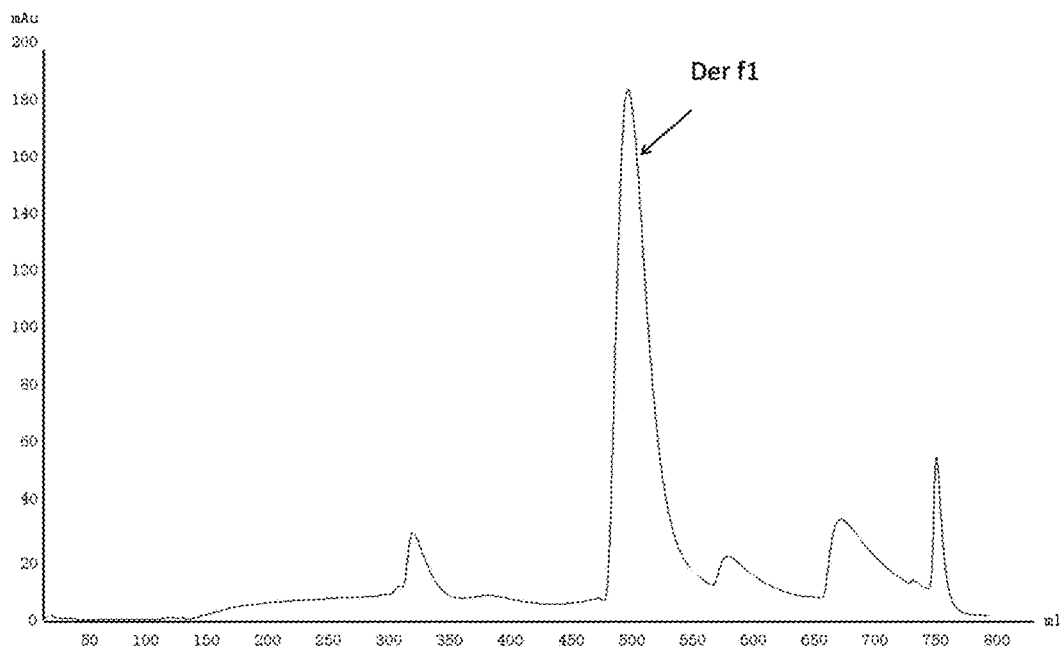
Figure 8B:
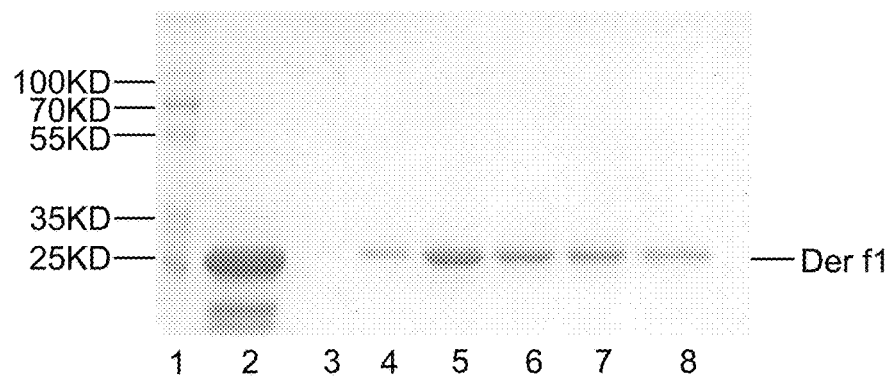

FIG. 8A is a chromatogram of the supernatant of proDer f1 fermentation broth by cation chromatography of the first step. FIG. 8B is the identification result of cation chromatography purification of the supernatant of proDer f1 fermentation broth, wherein lane 1 represents 11-100 KD non-pre-stained protein markers, lane 2 represents the supernatant of the proDer f1 fermentation broth before purification, lane 3 represents the flow-through liquid, and lanes 4-8 represent the elution of each tube.

Figure 9A:
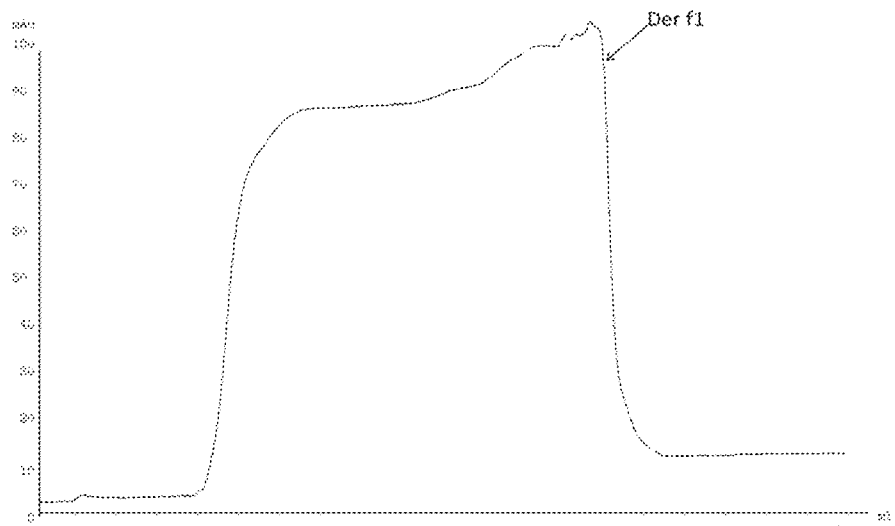
Figure 9B:
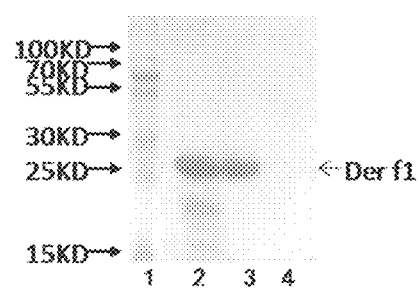

FIG. 9A is a chromatogram of Der f1 protein by anion chromatography of the second step, and FIG. 9B is a gel electrophoretogram.

FIG. 9A is a chromatogram of Der f1 protein by anion chromatography in step 2. FIG. 9B is the identification result of anion chromatography in the second step for proDerf1 protein purification, wherein lane 1 represents 11-100 KD non-pre-stained protein markers, lane 2 represents the supernatant before purification of Der f1 protein, lane 3 represents the flow-through liquid, and lane 4 represents elution peaks.

Figure 10A:
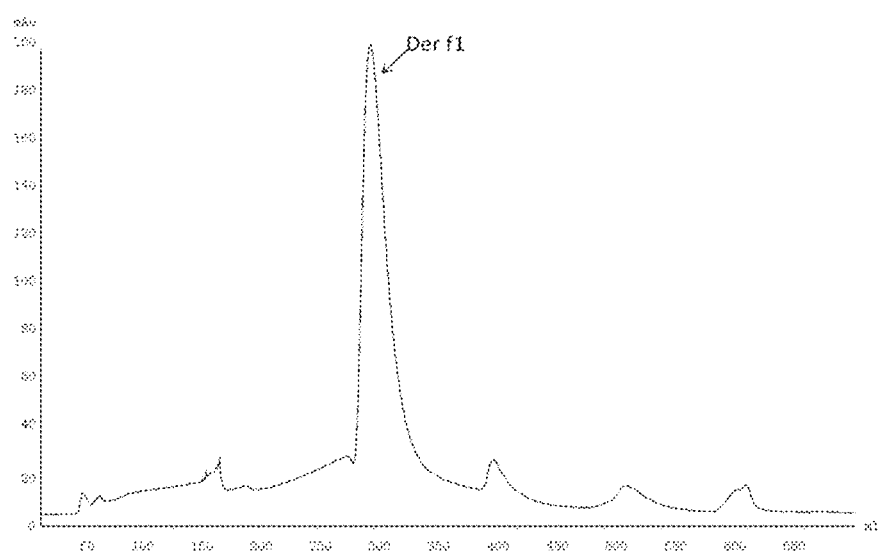
Figure 10B:
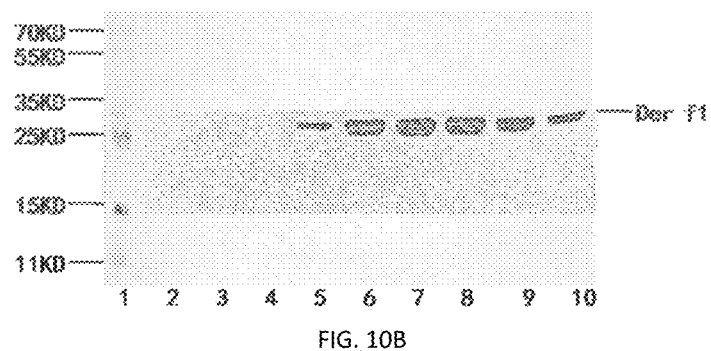

FIG. 10A shows a chromatogram of Der f1 protein by hydrophobic chromatography of the third step and FIG. 10B is a gel electrophoretogram.

FIG. 10A is a chromatogram of Der f1 protein by hydrophobic chromatography of the third step. FIG. 10B is a purification result of Der f1 protein by hydrophobic chromatography, wherein lane 1 represents 11-100 KD non-pre-stained protein markers, and lane 2-10 represent respective elution tubes.

Figure 11:
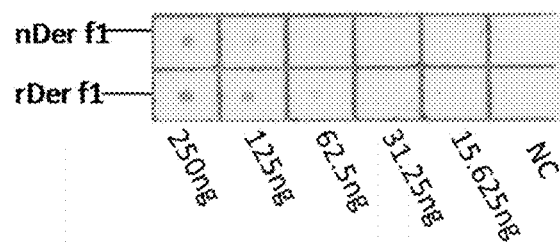

FIG. 11 is a comparison of reactivity to positive serum between recombinant Der f1 and natural Der f1, wherein nDerf1 represents the natural Der f1 protein, rDerf1 represents the recombinant Der f1 protein, and NC represents a PBS solution at pH 7.4.

Figure 12:
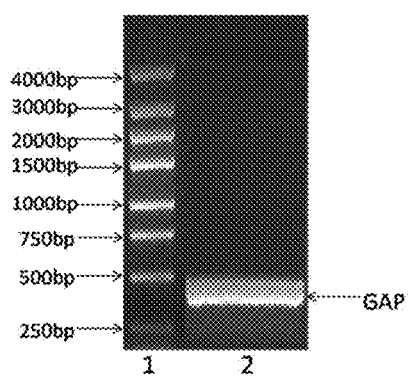

FIG. 12 is an agarose gel electrophoretogram of a PCR-amplified GAP gene, wherein lane 1 represents 250 bp DNA ladder and lane 2 represents the GAP gene.

Figure 13:
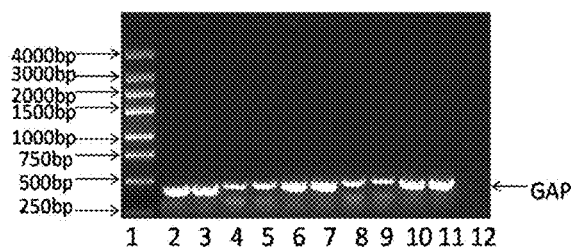

FIG. 13 is an agarose gel electrophoretogram of positive clone of GAP gene T-vector identified by PCR, wherein lane 1 represents 250 bp DNA ladder, lanes 2-11 represent positive clones obtained by blue-white screening, and lane 12 represents a negative clone obtained by blue-white screening.

Figure 14:
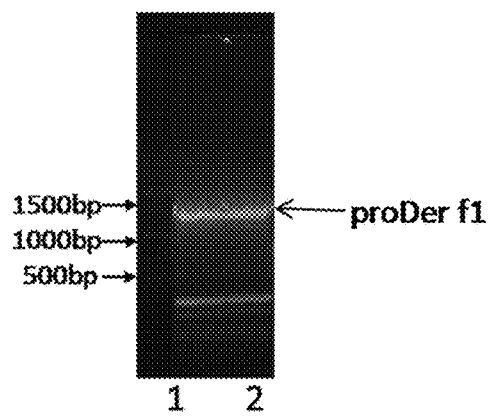

FIG. 14 is an agarose gel electrophoretogram of proDer f1 gene identified by PCR, wherein lane 1 represents 500 bp DNA ladder and lane 2 represents the proDer f1 gene.

Figure 15:
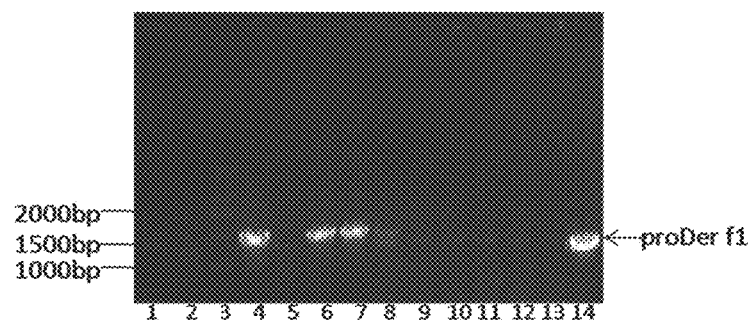

FIG. 15 is an agarose gel electrophoretogram for identifying T-vector positive clone of proDer f1 gene through PCR, wherein lane 1 and 2 represent negative clones obtained by blue-white screening, lanes 3 represents 500 bp DNA ladder, lanes 4-13 represent positive clones obtained by blue-white screening, and lane 14 represents a positive control (proDer f1 gene), in which line 4, 6, 7 are positive clones containing proDer f1 gene, other lines are false positive clones.

Figure 16A:
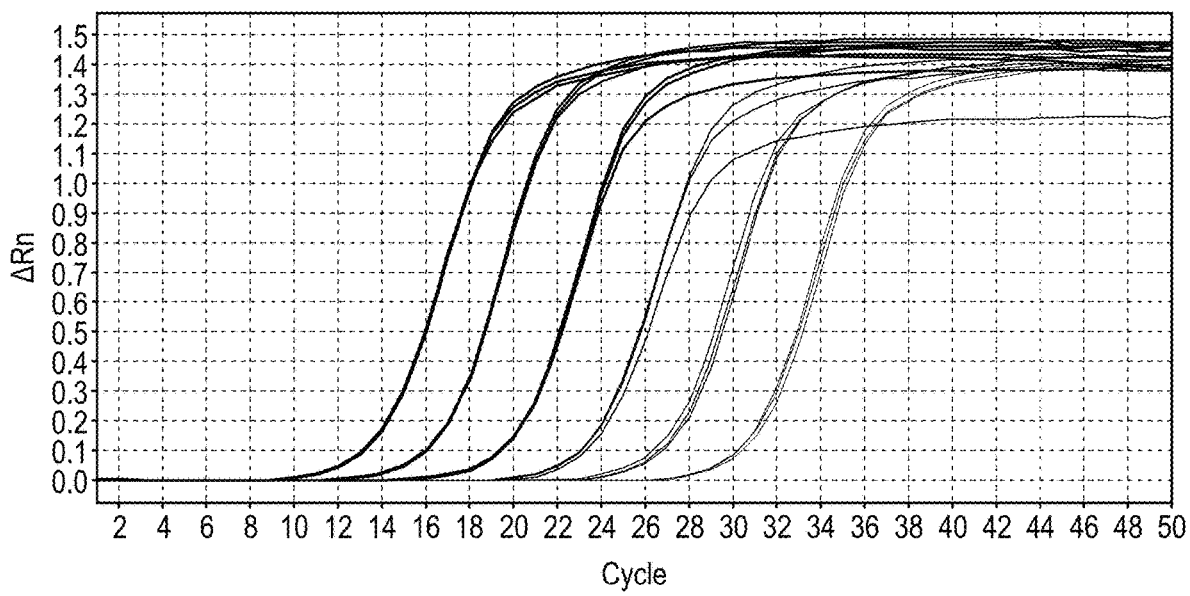
Figure 16B:
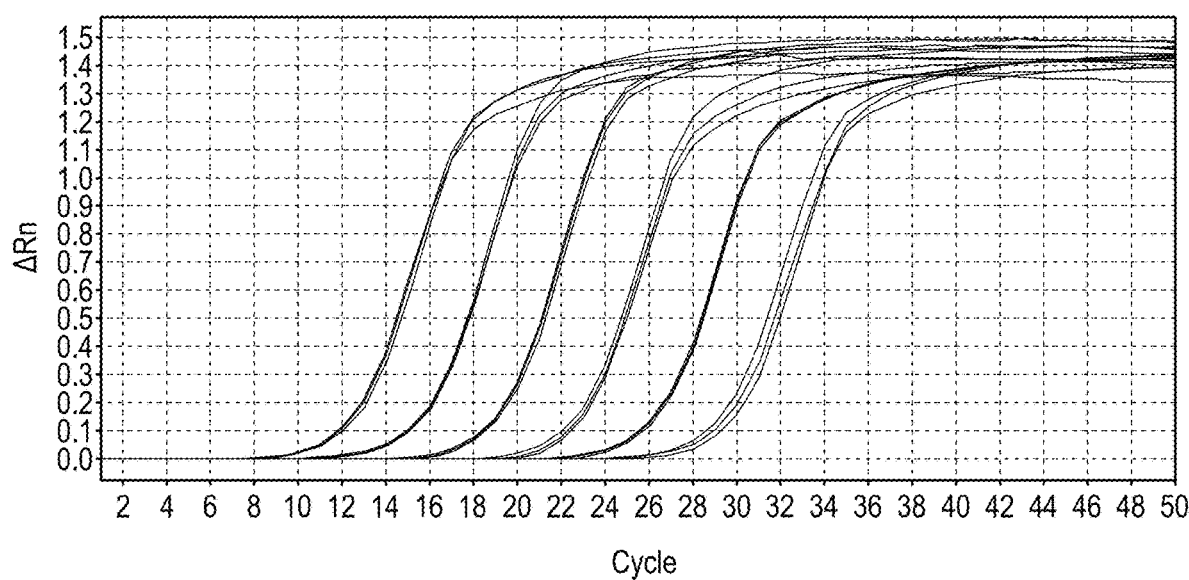

FIGS. 16A and 16B show amplification curves of a standard plasmid.

FIG. 16A shows amplification curves of the standard plasmid T-GAP, and FIG. 16B shows amplification curves of the standard plasmid T-proDer f1.

Figure 17A:
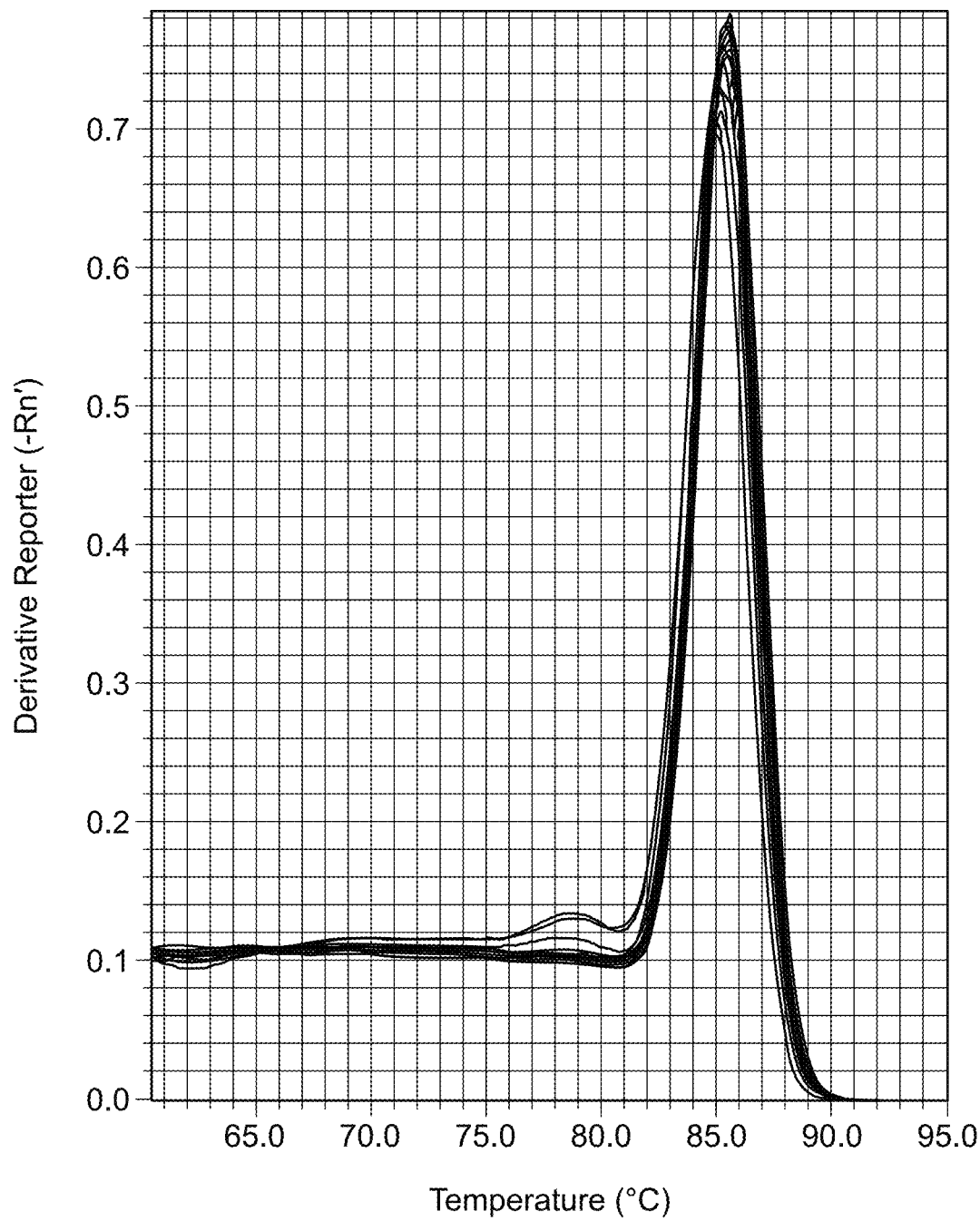
Figure 17B:
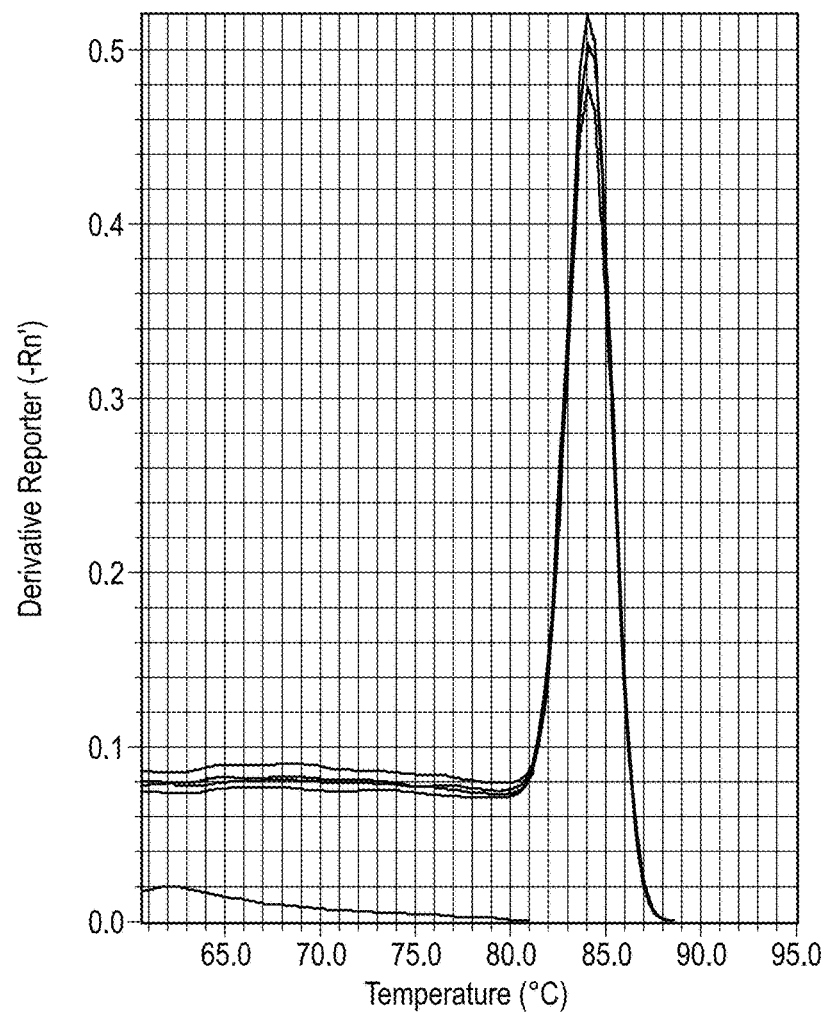

FIGS. 17A and 17B show melting curves of a standard plasmid.

FIG. 17A shows melting curves of the standard plasmid T-GAP, and FIG. 17B shows melting curves of the standard plasmid T-proDer f1.

Figure 18A:
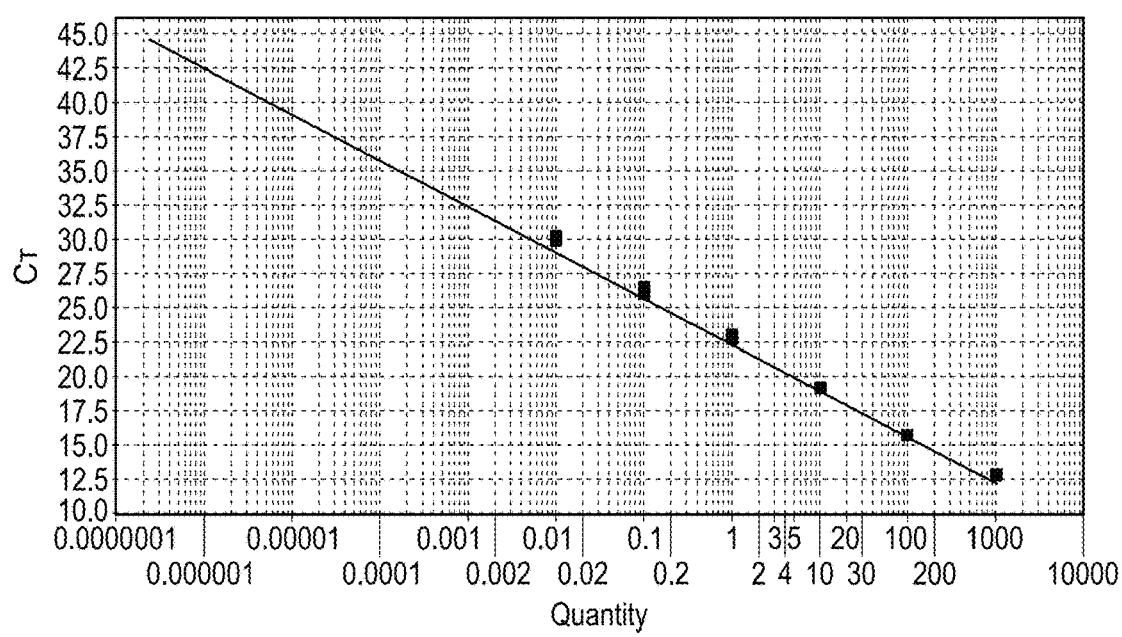
Figure 18B:
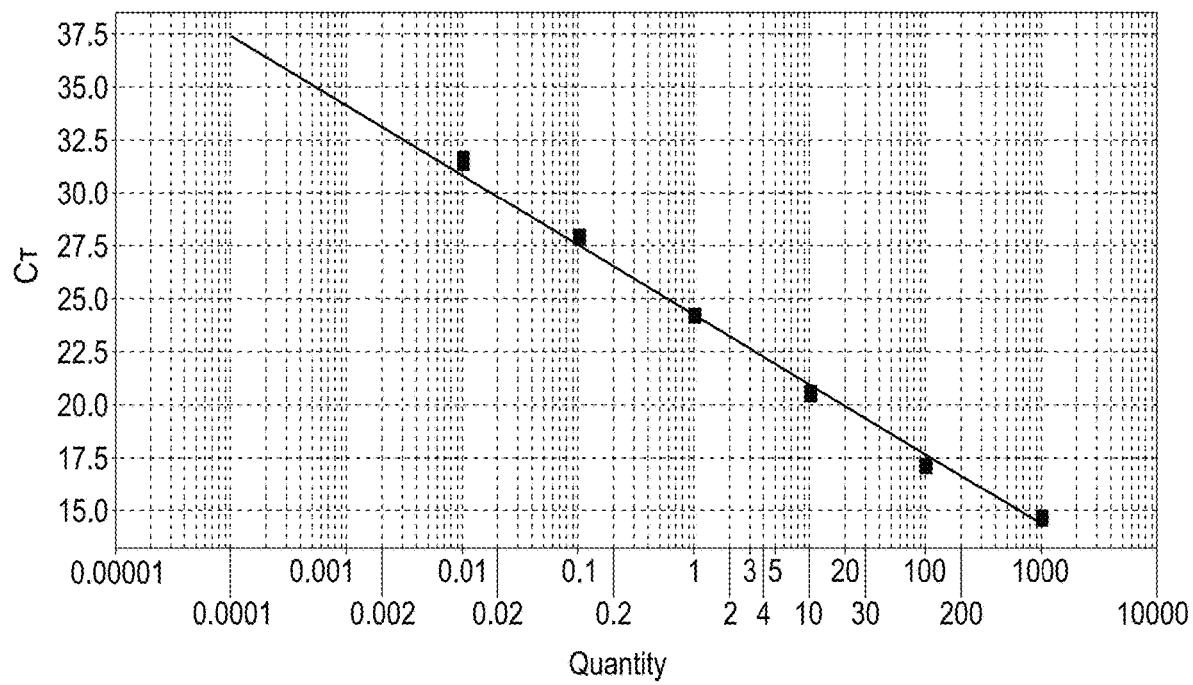

FIGS. 18A and 18B show a standard curve of a standard plasmid.

FIG. 18A shows a standard curve of the standard plasmid T-GAP, and FIG. 18B shows a standard curve of the standard plasmid T-proDer f1.

Figure 19A:
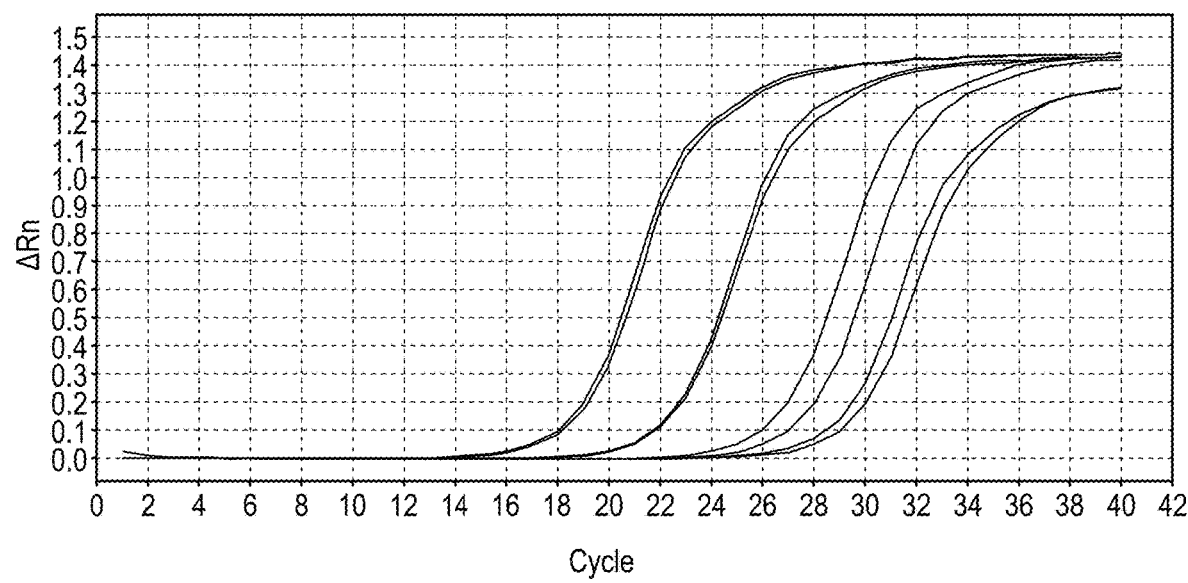
Figure 19B:
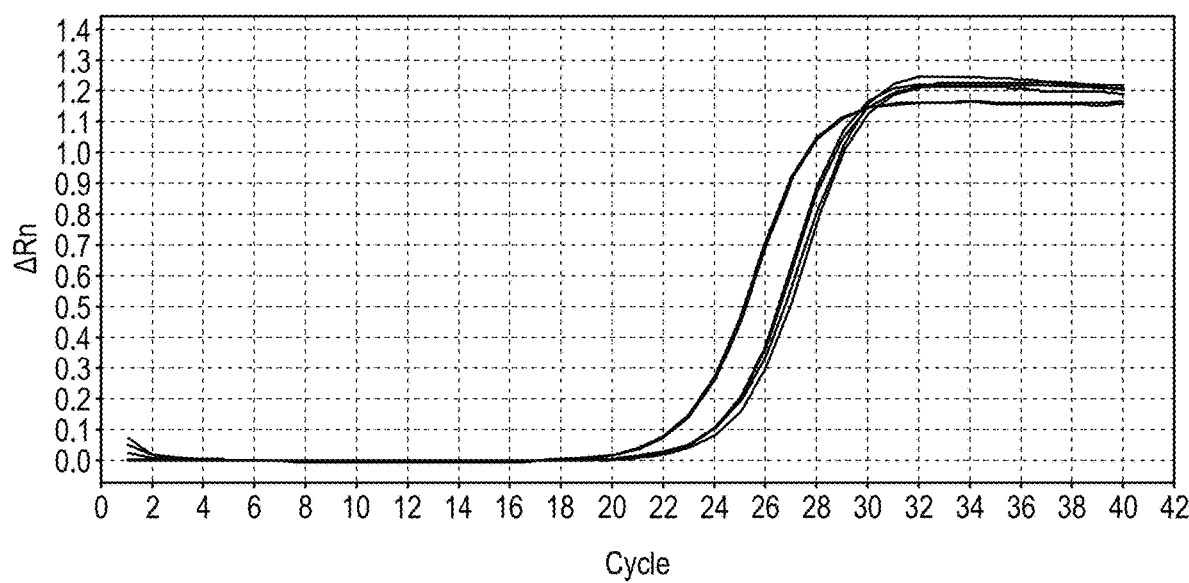

FIGS. 19A-19B show amplification curves of samples to be tested.

FIG. 19A shows amplification curves obtained when the samples to be tested are amplified with GAP-1 and GAP-2 as primers, and FIG. 19B shows amplification curves obtained when the samples to be tested are amplified with 5'AOX and 3'AOX as primers.

Figure 20A:
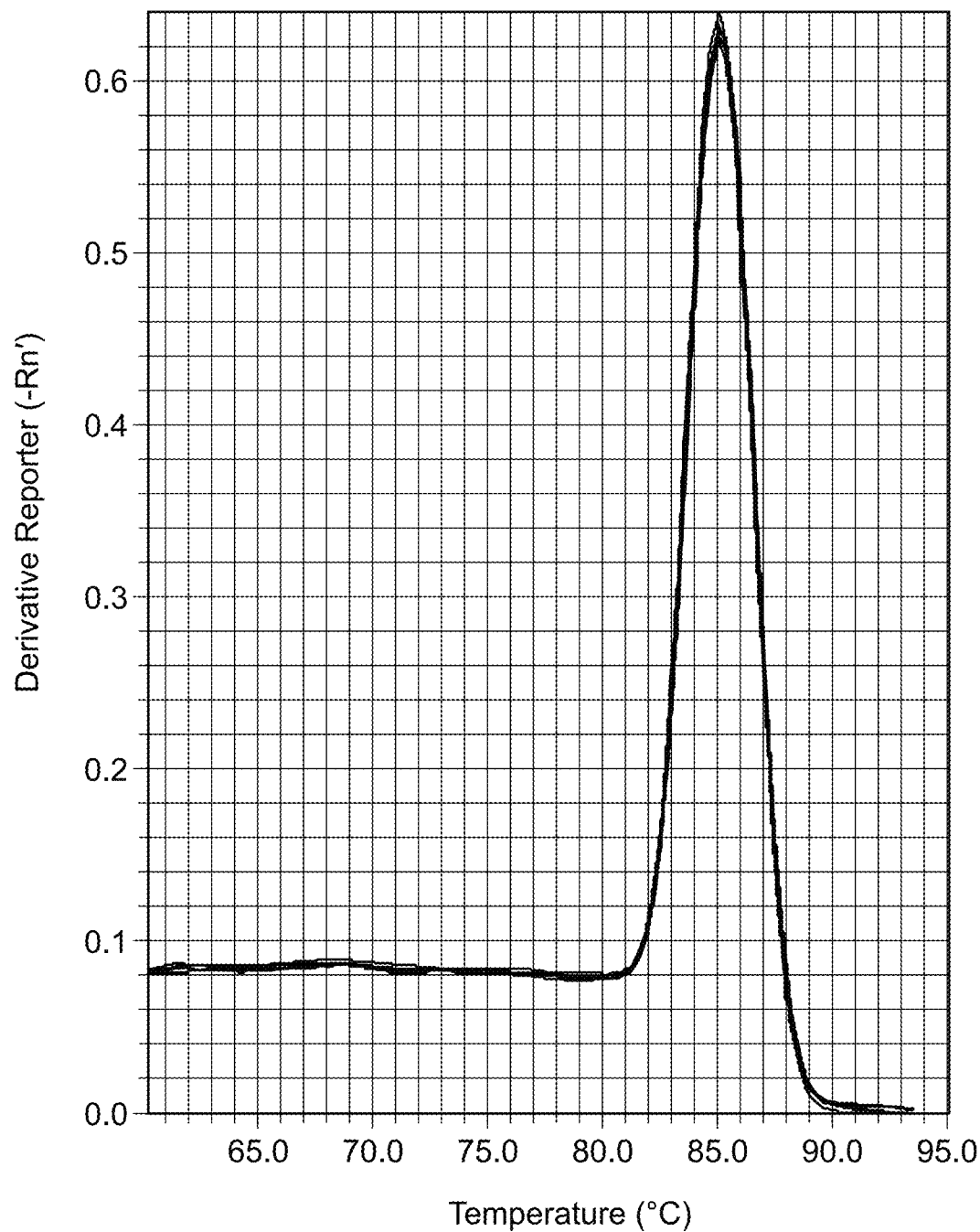
Figure 20B:
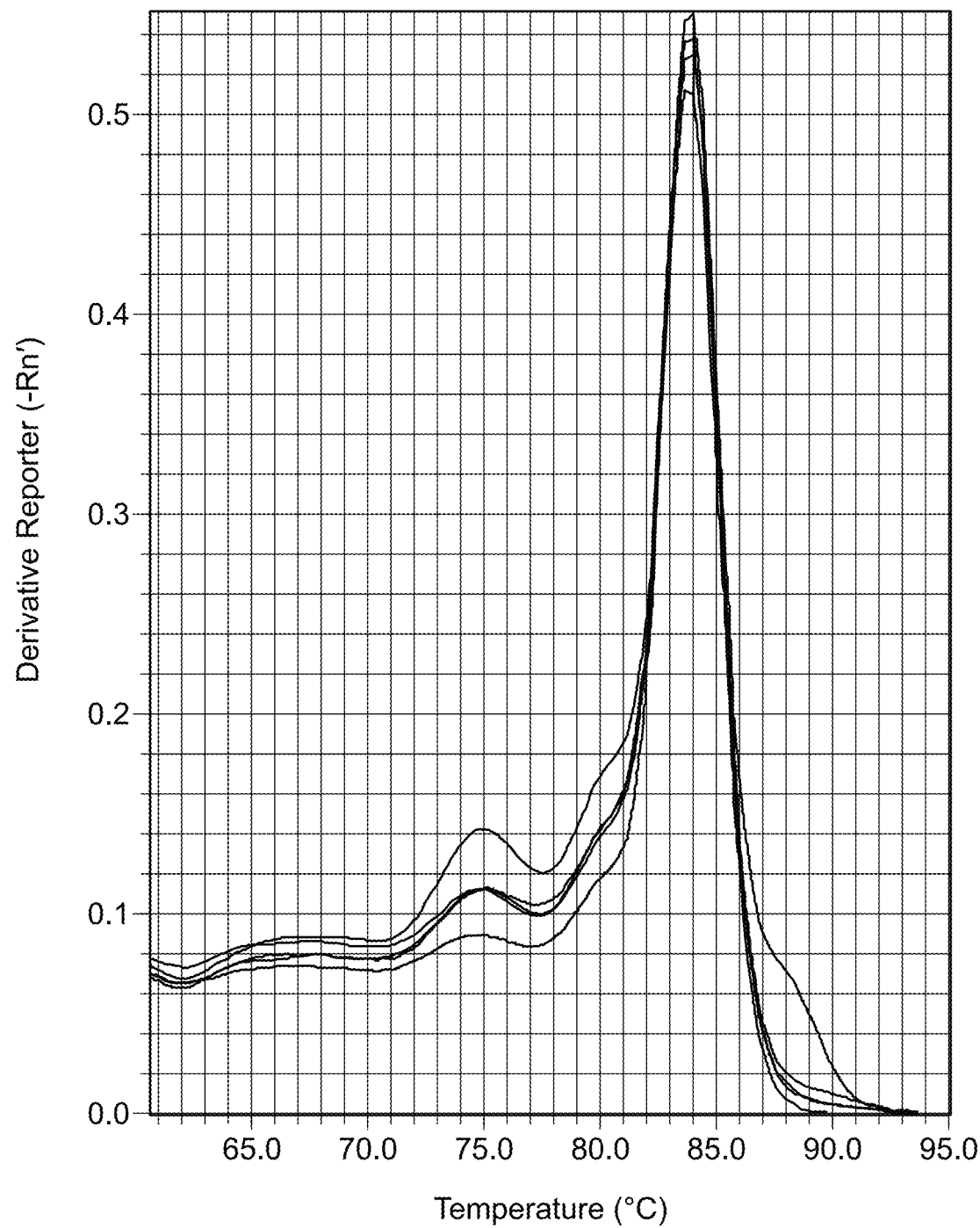

FIGS. 20A and 20B show melting curves of samples to be tested.

FIG. 20A shows melting curves obtained when the samples to be tested are amplified with GAP-1 and GAP-2 as primers, and FIG. 20B shows melting curves obtained when the samples to be tested are amplified with 5'AOX and 3'AOX as primers.

DETAILED DESCRIPTION OF THE INVENTION

The invention is further illustrated below in conjunction with specific examples. It should be understood that the examples referred to are merely illustrative of the invention and are not intended to limit the scope of the present invention.

Example 1 Codon Optimization of Recombinant ProDer f1

Based on the DNA sequence of proDer f1 disclosed in GenBank (GenBank accession no. AB034946.1), as shown in SEQ ID No: 2, the inventors performed codon optimization of the gene to obtain the proDer f1 gene of the present invention of which the nucleotide sequence is as shown in SEQ ID No: 1 and the amino acid sequence is as shown in SEQ ID No: 3. Comparison of each parameter before and after codon optimization of the proDer f1 is as follows:

1. Codon Adaptation Index (CAI)

As can be seen from FIG. 2A, the codon adaptation index (CAI) of the original proDer f1 gene in the *Pichia pastoris* expression system before codon optimization is 0.76. As can be seen from FIG. 2B, the proDer f1 gene has a CAI index of 0.85 in the *Pichia pastoris* expression system after codon optimization. Usually, when CAI=1, it is considered that the gene is in the most ideal expression state in the expression system. The lower the CAI index, the worse the expression level of the gene in the host. Thus, it can be seen the gene sequence obtained by codon optimization can increase the expression level of the proDer f1 gene in the *Pichia pastoris* expression system.

2. Optimal Codon Usage Frequency (POP)

As can be seen from FIG. 3A, based on the *Pichia pastoris* expression vector, the occurrence percentage of the low-utilization codon (codon with a utilization rate less than 40%) of the proDer f1 gene sequence is 10% before codon optimization. This unoptimized gene uses tandem rare codons that may reduce translation efficiency and even disintegrate a translation assembly. As can be seen from FIG. 3B, the proDer f1 gene has a low utilization codon frequency of 0 in the *Pichia pastoris* system after codon optimization.

3. GC Base Content (GC Curve)

The ideal distribution region of GC content is 30%-70%, and any peak outside this region will affect transcription and translation efficiency to varying degrees. As can be seen from the comparison of the average GC base content distribution region plots of the proDer f1 gene in FIG. 4A and FIG. 4B, FIG. 4A shows the average GC base content of the proDer f1 gene being 41.85%, and FIG. 4B shows that the peaks of GC content appearing outside the 30%-70% region are removed after optimization, and finally the average GC base content of optimized proDer f1 is 42.80%.

Example 2: Construction of an Expression Plasmid Containing the ProDer f1 Gene

A sequence of XhoI restriction site was introduced at the 5' end, and a sequence of NotI restriction site was introduced at the 3' end of the codon-optimized proDer f1, and then full gene synthesis was performed. The synthesized gene fragment was constructed into the pUC57 plasmid supplied by GenScript (Nanjing) Co., Ltd., thereby obtaining a plasmid for long-term preservation, denoted as pUC57-proDer f1 plasmid.

PCR amplification was performed using the pUC57-proDer f1 plasmid as a template, and primers of following sequences:

```
upstream primer (SEQ ID No: 5):
M13 F:
TGT AAA ACG ACG GCC AGT downstream primer (SEQ ID No: 6):
M13 R:
CAG GAA ACA GCT ATG AC
```

The total volume of the reaction was 50 μL, in which 2.5 μL of each primer at a concentration of 10 μmol/L was added, 1 μL of dNTP at a concentration of 10 mmol/L was added, and 0.5 μL DNA polymerase being Q5 (#M0491L, purchased from New England BioLabs) at 2 U/pt was added. The reaction conditions were 98° C. for 5 seconds, 55° C. for 45 seconds, and 72° C. for 30 seconds. After 25 cycles, the product was analyzed by 1.0% agarose gel electrophoresis. The results showed that the product size was consistent with the expected size (915 bp) (results as shown in FIG. 5). The product was digested with XhoI (#R0146S, purchased from New England BioLabs) and NotI (#R0189S, purchased from New England BioLabs), respectively, and electrophoresed on 1% agarose gel to obtain a gene product, which was purified using a DNA gel recovery kit (DP214, purchased from Tiangen Biotech (Beijing) Co., Ltd.). The purified product was ligated to pPICZαA plasmid (V173-20, purchased from Invitrogen) with T4 ligase (#M0202S, purchased from New England BioLabs), and transformed into DH5a competent cells (CB101, purchased from Tiangen Biotech (Beijing) Co., Ltd.) and cultured in an LB solid medium containing bleomycin (purchased from Invitrogen) at 37° C. overnight. On the second day, the positive clones were picked and sequenced, and the sequence was found identical to the expected sequence by alignment, thereby obtaining the expression plasmid of codon-optimized proDer f1, denoted as pPICZα-proDer f1 (the plasmid construction was as shown in FIG. 6).

Example 3: Construction of a *Pichia pastoris* Host Engineering Strain Containing a Recombinant ProDer f1 Gene Formulation of YPDS solid medium: the medium was formulated according to the instructions of Easy SelectPichia Expression Kit, Invitrogen, comprising 10 g/L yeast extract, 20 g/L peptone, 20 g/L glucose, 15 g/L agarose, and 182 g/L sorbitol.

1. Construction of a Host Engineering Strain Containing Codon-Optimized proDer f1

Electrocompetent cells were prepared according to the method of instructions of Easy SelectPichia Expression Kit, Invitrogen. The plasmid pPICZα-proDer f1 obtained in Example 2 was linearized with Sac I restriction endonuclease (#R0156S, purchased from New England Biolabs), and precipitated with ethanol. The linearized vector was electrotransformed into competent cells of *Pichia pastoris* X33. The cells were plated on YPDS solid media and cultured at 30° C. until the transformants grew.

Example 4: Inducible Expression and Identification of Engineering Strains Containing Codon-Optimized ProDer f1 Gene Formulation of BMGY medium: the medium was formulated according to the instructions of Easy SelectPichia Expression Kit, Invitrogen, comprising 10 g/L yeast extract, 20 g/L peptone, 3 g/L $K_2HPO_4$, 11.8 g/L $KH_2PO_4$, 13.4 g/L YNB, $4 \times 10^{-4}$ g/L biotin, and 10 g/L glycerin.

Formulation of BMMY medium: the medium was formulated according to the instructions of Easy SelectPichia Expression Kit, Invitrogen, comprising 10 g/L yeast extract, 20 g/L peptone, 3 g/L $K_2HPO_4$, 11.8 g/L $KH_2PO_4$, 13.4 g/L YNB, $4 \times 10^{-4}$ g/L biotin, and 5 mL/L methanol.

1. Methanol-Induced Expression of an Engineering Strain of Codon-Optimized proDer f1

The host monoclonal engineering strain obtained in Example 3 was picked into a 5 mL BMGY medium and cultured in a 50 mL sterile centrifuge tube at 30° C. and 220 rpm until $OD_{600}$ reaches 1.0-2.0. 1 mL of the culture was stored, and the remaining strain solution was resuspended and transferred to BMMY for induced expression at a small scale, and methanol was supplemented every 24 hours to a final concentration of 1%. One week later, the supernatant of the strain solution was collected by centrifugation, and analyzed by SDS-PAGE gel electrophoresis and Western blotting. Brightness of expressed product bands was observed. FIGS. 7A and 7B are plots of identification of induced expression of gene engineering strains containing proDer f1. As seen from FIGS. 7A and 7B, the proDer f1 protein was significantly expressed in the engineering strain.

Example 5: Purification of Recombinant ProDer f1 Protein

The Der f1 constructed in this invention is obtained mainly by ion exchange and hydrophobic chromatography purification methods. HiTrap SP FF, HiTrap Q FF, and HiTrap Phenyl HP were selected as the chromatographic packings. The specific steps are as follows:

1. Pretreatment of the Fermentation Broth by Impurity Removal

The fermentation broth of host engineering strain containing proDer f1 obtained according to Example 4 was centrifuged at a low temperature at 12000 rpm for 15 minutes to collect a supernatant, and the supernatant was dialyzed in a 5 KD dialysis bag against a 25 mM sodium acetate buffer at pH 4.5 for 48 h, and filtered through a 0.45 μm filter membrane to obtain a supernatant of the treated fermentation broth.

2. Cation Exchange Chromatography

The treated fermentation broth of the previous step was loaded on a SPFF cation exchange chromatographic column, wherein the equilibration buffer was 50 mM NaAc at pH 4.5, the elution buffer was 50 mMNaAc and 1.0 M NaCl at pH 4.5, isocratic elution was performed at 12%, 25% and 100%, and the sample peaks were mainly concentrated at the 25% elution peak. FIG. 8A is an ion exchange purification chromatogram of Der f1, and FIG. 8B is an SDS-PAGE analysis plot of Der f1 after ion exchange chromatography.

3. Anion Exchange Chromatography

The Der f1 protein peak purified in the previous step was collected, and the sample was ultrafiltrated with a 20 mM $NaH_2PO_4$ solution at pH 6.0, and loaded on a HiTrap Q FF chromatography packing. The equilibration buffer was 20 mM $NaH_2PO_4$ at pH 6.0, and the elution buffer was 20 mM $NaH_2PO_4$ and 1.0 M NaCl at pH 6.0. The flow-through peak of Der f1 was collected. The flow-through peak of Der f1 protein was as shown in FIGS. 9A and 9B.

4. Hydrophobic Chromatography

The flow-through peak of Der f1 from the anion chromatography was collected, and ammonium sulfate was added to a final concentration of 1.5 M. The fermentation broth supernatant treated as above was loaded on a Phenyl HP chromatographic column. The equilibration buffer was 20 mM $NaH_2PO_4$ and 1.5 M $(NH_4)_2SO_4$ at pH 6.0; the elution buffer was 20 mM $NaH_2PO_4$ at pH 6.0, isocratic elution was performed at 25%, 50%, 70%, and 100%, and the Der f1 protein is mainly concentrated at the 75% elution peak. FIG. 10A is hydrophobic chromatography purification chromatogram of Der f1, and FIG. 10B is an SDS-PAGE analysis plot of Der f1 after hydrophobic chromatography. The yield of target protein per liter of fermentation broth is as high as 200 mg or more.

Example 6: Analysis of Der f1 Protein Activity

The purified Der f1 protein was dialyzed against a PBS buffer at pH 7.4, and the protein concentration was determined by a Pierce BCA protein concentration assay kit (Cat No: 23225, purchased from Pierce), and fold-diluted to 250 ng, 125 ng, 62.5 ng, 31.25 ng, and 15.625 ng. The obtained solution was detected for the reactivity with sera of patients allergic to *Dermatophagoides farinae* by comparing with natural Der f1. FIG. 11 shows that the recombinant Der f1 has substantially identical reactivity with the sera as compared with the natural Der f1, showing that the recombinant Der f1 has a similar biological activity as the natural Der f1.

Example 7: Determination of Gene Copy Number of Recombinant ProDer f1 Engineering Strain 1. Inoculation in X33 strain: the strains were cultured in YPD media for 24 h, the X33 genome was extracted by a genomic extraction kit (purchased from Tiangen Biotech (Beijing) Co., Ltd.), and GAP gene was amplified using the X33 genome as a template, and GAP-1 and GAP-2 as primers of which the sequences are as follows:

```
upstream primer
                            (SEQ ID No: 7)
GAP-1:
GGTATTAACGGTTTCGGACGTATTG downstream primer
                            (SEQ ID No: 8)
GAP-2:
GATGTTGACAGGGTCTCTCTCTTGG
```

The total volume of the reaction was 50 μL, in which 2.5 μL of each primer at a concentration of 10 μmol/L was added, 1 μL of dNTP at a concentration of 10 mmol/L was added, and 0.5 μL DNA polymerase being Taq DNA Polymerase (M0267S, purchased from New England BioLabs) at 2 U/μL was added. The reaction conditions were 94° C. for 10 minutes, 94° C. for 30 seconds, 55° C. for 30 seconds, 68° C. for 60 seconds, and 68° C. for 5 minutes. After 30 cycles, the product was analyzed by 1.0% agarose gel electrophoresis. The results showed that the product size was consistent with the expected size (400 bp) (results as shown in FIG. 12). The obtained gene product was purified by DNA gel recovery kit (DP214, purchased from Tiangen Biotech (Beijing) Co., Ltd.) and 2× buffer ligated into pGM-T vector kit (VT202-01, purchased from Tiangen Biotech (Beijing) Co., Ltd.). The vector was transformed into the Top10 competent cells (CB104, purchased from Tiangen Biotech (Beijing) Co., Ltd.), and cultured at 37° C. overnight on blue-white screening media. On the next day, white clones were picked and identified by PCR for which the primers used were GAP-1 and GAP-2. The PCR reaction conditions were consistent with the above-mentioned conditions. The obtained product was analyzed by 1.0% agarose gel electrophoresis, and the results showed that the product size is consistent with the expected size (400 bp) (results as shown in FIG. 13). The positive clones were sent to GenScript (Nanjing) Co., Ltd. for sequencing, and the sequence was found completely identical to the expected sequence by alignment, thereby obtaining the T vector clone of GAP gene, denoted as T-GAP. The T-GAP clone having a correct sequence was inoculated in an LB liquid medium at 37° C. overnight, and the plasmid was extracted (using a plasmid mini-extract kit DP103, purchased from Tiangen Biotech (Beijing) Co., Ltd.) to obtain a standard plasmid for real-time quantitative PCR.

2. The proDer f1 gene was amplified using the pPICZα-proDer f1 plasmid of Example 2 as a template, and 5' AOX and 3' AOX as primers with the following sequences:

```
upstream primer (SEQ ID No: 9):
5' AOX:
GACTGGTTCCAATTGACAAGC downstream primer (SEQ ID No: 10):
3' AOX:
GGCAAATGGCATTCTGACAT
```

The total volume of the reaction was 50 in which 2.5 μL of each primer at a concentration of 10 μmol/L was added, 1 μL of dNTP at a concentration of 10 mmol/L was added, and 0.5 μL DNA polymerase being Taq DNA Polymerase (# M0267S, purchased from New England BioLabs) at 2 U/μL was added. The reaction conditions were 94° C. for 10 minutes, 94° C. for 30 seconds, 49° C. for 30 seconds, and 68° C. for 60 seconds, and 68° C. for 5 minutes. After 30 cycles, the product was analyzed by 1.0% agarose gel electrophoresis. The results showed that the product size was consistent with the expected size (1500 bp) (results as shown in FIG. 14). The obtained gene product was purified by DNA gel recovery kit (DP214, purchased from Tiangen Biotech (Beijing) Co., Ltd.) and ligated into pGM-T vector kit (VT202-01, purchased from Tiangen Biotech (Beijing) Co., Ltd.). The vector was transformed into the Top10 competent cells (CB104, purchased from Tiangen Biotech (Beijing) Co., Ltd.), and cultured at 37° C. overnight on blue-white screening media. On the next day, white clones were picked and identified by PCR for which the primers used were 5'AOX and 3'AOX. The PCR reaction conditions were consistent with the above-mentioned conditions. The obtained product was analyzed by 1.0% agarose gel electrophoresis, and the results showed that the product size is consistent with the expected size (1500 bp) (results as shown in FIG. 15). The positive clones were sent to GenScript (Nanjing) Co., Ltd. for sequencing, and the sequence was found completely identical to the expected sequence by alignment, thereby obtaining the T vector clone of proDer f1, denoted as T-proDer f1. The T-proDer f1 clone having a correct sequence was inoculated in an LB liquid medium at 37° C. overnight, and the plasmid was extracted using a plasmid mini-extract kit (DP103, purchased from Tiangen Biotech (Beijing) Co., Ltd.) to obtain a standard plasmid for real-time quantitative PCR.

3. Calculation of Gene Copy Number:

The concentration (ng/μL) of the standard plasmid was determined by a nucleic acid microanalyzer (Nanodrop2000, ThermoFisher). Copy numbers of GAP and proDer f1 were calculated according to the following formula:

$$\text{Copies}/u = (6.02 \times 10^{23}) \times (\text{ng}/\mu \text{l} \times 10^{-9})/(\text{DNA length} \times 660)$$

4. Processing Samples to be Tested

The pPICZα-proDer f1-X33 engineering strain was inoculated in YPD liquid media at 30° C. overnight; and the genome was extracted the next day, and its concentration (ng/μL) and purity were determined by a nucleic acid quantitative microanalyzer.

5. Establishment of a Standard Curve

The standard plasmids of T-GAP and T-proDer f1 with known copy numbers were gradiently diluted to $10^8$, $10^7$, $10^6$, $10^5$, $10^4$, and $10^3$ copies/μl, respectively. The fluorescent quantitative PCR were performed using GAP-1 and GAP-2, 5' AOX and 3' AOX as primers, respectively. FIG. 16A shows amplification curves of the standard plasmid T-GAP, FIG. 16B shows amplification curves of the standard plasmid T-proDer f1, FIG. 17A shows melting curves of the standard plasmid T-GAP, and FIG. 17B shows melting curves of the standard plasmid T-proDer f1. Each gradient was assayed 3 times to verify the repeatability of the standard curve. Standard curves were established with the Ct values as the ordinate and the starting template copy numbers as the abscissa. FIG. 18A shows a standard curve of the standard plasmid T-GAP, and FIG. 18B shows a standard curve of the standard plasmid T-proDer f1.

6. Determination of Copy Number of ProDer f1 Gene in Recombinant Strains

The genome sample of extracted pPICZα-proDer f1-X33 was serially 10-fold-diluted to obtain four gradients of stock solution, $10^{-1}$, $10^{-2}$, and $10^{-3}$. Fluorescent quantitative PCR was performed using GAP-1 and GAP-2, 5' AOX and 3' AOX as primers, and each gradient was assayed three times. FIG. 19A shows amplification curves of the samples to be tested with GAP-1 and GAP-2 as primers, FIG. 19B shows amplification curves of the samples to be tested with 5' AOX and 3' AOX as primers, FIG. 20A shows melting curves of the samples to be tested with GAP-1 and GAP-2 as primers, and FIG. 20B shows melting curves of the samples to be tested with 5' AOX and 3' AOX as primers. The GAP gene exists in *Pichia pastoris* in a single copy. Therefore, the copy number of the GAP gene can be used to characterize the initial copy number of the genome in the template. The ratio of the copy number of the proDer f1 gene to the copy number of the GAP gene is the copy number of proDer f1 gene in the *Pichia pastoris* genome. Table 1 shows the detection results of copy number of the proDer f1 gene in the *Pichia pastoris* gene engineering strain, the detected copy number is between 4.85 and 6.02, and finally the copy number of the proDer f1 gene in the recombinant strain was averaged to eliminate the system error and determined to be 5.

TABLE 1

Results of copy number of proDer f1 in the genome detected by real-time fluorescent quantitative PCR Average Ct value gene copy number ($10^N$)Copy number of proDer f1 gene in *Pichia pastoris* genome

| DNA concentration | GAP gene | proDer f1 gene | GAP gene | proDer f1 gene | Copy number of the proDer f1 gene/copy number of the GAP gene |
|---|---|---|---|---|---|
| Stock solution | 18.802 | 23.000 | 6.84 | 5.96 | 6.02 |
| $10^{-1}$ | 19.939 | 24.382 | 6.29 | 5.57 | 5.46 |
| $10^{-2}$ | 23.650 | 24.704 | 5.17 | 5.29 | 5.07 |
| $10^{-3}$ | 27.966 | 24.876 | 3.62 | 5.19 | 4.85 |

Example 8: Analysis of the Acting Elements in the ProDer f1 Genome

There is no stable additional plasmid in *Pichia pastoris*, the expression vector is homologously recombined with the host chromosome, and the exogenous gene expression framework is fully integrated into the chromosome to realize the expression of the exogenous gene; the typical *Pichia pastoris* expression vector contains a regulatory sequence of alcohol oxidase gene, and contains the main structures comprising AOX promoter, multiple cloning site, transcription termination and polyA formation gene sequence (TT), screening markers and the like. The promoter is a cis-element for gene expression regulation and an important element for the genetically engineered expression vector. The important role of the promoter at the transcriptional level determines the gene expression level.

The proDer f1 genome was extracted according to the method of Example 7, and the proDer f1 gene was amplified from the genome using 5' AOX and 3' AOX as primers. The obtained samples were sent to GenScript (Nanjing) Co., Ltd. to detect the acting element before and after the proDer f1 gene which was inserted into the genome. The results of genome sequencing indicated that the proDer f1 gene expression framework was integrated into the chromosome of *Pichia pastoris* by a single cross-insertion, which enabled the proDer f1 gene to express the gene using the AOX promoter on the yeast chromosome, and thus the expression level was higher.

Generally, the closer the first ATG of the exogenous coding sequence to the ATG of AOX1, the better the expression effect. In the gene construction, the inventors chose an enzyme cleavage site closest to the ATG of AOX1, and found that the proDer f1 gene was away from ATG of AOX1 only by 242 bp. In addition, the alpha-factor signal peptide and Kozak sequence GCCACCATGG were added in front of proDer f1 gene, and the signal peptide and the sequence can greatly improve transcription and translation efficiency and increase expression efficiency of proDer f1 gene in eukaryotes.

The invention claimed is:

1. An isolated DNA sequence encoding a propeptide of Der f1 protein (proDer f1 protein) having a base sequence as shown in SEQ ID NO: 1, wherein the DNA sequence is comprised in a vector.

2. The DNA sequence of claim 1, wherein the DNA sequence is comprised in the vector pAO815, pPIC9, pPIC9K, pPIC3.5, pPIC3.5K, pPICZα A, B, C or pGAPZα A, B, C.

3. The DNA sequence of claim 2, wherein the vector is comprised in the *Pichia pastoris* strain SMD1168, GS115, KM71, X33 or KM71H.

4. The DNA sequence of claim 3, wherein there is 242 bp interval between the DNA sequence encoding proDer f1 protein and the ATG of AOX1 on *Pichia pastoris*; and the DNA sequence encoding the proDer f1 protein is preceded by an alpha-factor signal peptide and Kozak sequence GCCACCATGG.

* * * * *

SEQUENCE LISTING

<160> NUMBER OF SEQ ID NOS: 10

<210> SEQ ID NO 1
<211> LENGTH: 912
<212> TYPE: DNA
<213> ORGANISM: Dermatophagoides farinae

<400> SEQUENCE: 1

| | | | | | | |
|---|---|---|---|---|---|---|
| agaccagcat | ctatcaagac | atttgaagag | ttcaagaaag | cttttaacaa | gaactacgcc | 60 |
| actgttgaag | aggaagaggt | cgctagaaag | aacttttttgg | aatctttgaa | gtatgttgag | 120 |
| gcaaacaaag | gtgctattaa | tcacttgtct | gatttgtccc | ttgacgaatt | caagaacaga | 180 |
| tacttgatga | gtgctgaagc | ctttgagcaa | ttgaaaacac | agttcgacct | taacgccgaa | 240 |
| acctcagcat | gtagaattaa | ctcagttaat | gtccctagtg | agtggatct | tagaagtttg | 300 |
| agaaccgtta | ctcctattag | aatgcaaggt | ggatgtggtt | cttgctgggc | cttctccgga | 360 |
| gttgcagcta | ccgaatctgc | ttacttggcc | tacagacaga | cttcattgga | tcttagtgaa | 420 |
| caagagttgg | ttgactgtgc | ttcccagcat | ggttgccacg | gagacactat | tcctagaggt | 480 |
| attgaataca | tccaacagaa | cggagttgtc | gaagagagat | catacccata | tgttgctaga | 540 |
| gagcaacagt | gtagaagacc | taactcacaa | cactacggta | ttagtaacta | ctgccagatc | 600 |
| tatccacctg | atgttaagca | aattagagaa | gcattgacac | agacccatac | tgcaattgct | 660 |
| gtcattatcg | gaatcaagga | tttgagagct | ttccaacatt | acgacggtag | aacaattatc | 720 |
| caacacgata | acgatacca | gccaaattat | catgctgtta | acattgtcgg | ttacggatcc | 780 |
| acccaaggtg | ttgattattg | gatcgtcaga | aactcttggg | atactacatg | gggtgattct | 840 |
| ggttacggat | atttccaagc | tggaaacaat | ttgatgatga | ttgaacagta | cccttatgtt | 900 |
| gtcatcatgt | aa | | | | | 912 |

<210> SEQ ID NO 2
<211> LENGTH: 912
<212> TYPE: DNA
<213> ORGANISM: Dermatophagoides farinae

<400> SEQUENCE: 2

| | | | | | | |
|---|---|---|---|---|---|---|
| cgtccagctt | caatcaaaac | ttttgaagaa | ttcaaaaaag | ccttcaacaa | aaactatgcc | 60 |
| accgttgaag | aggaagaagt | tgcccgtaaa | aacttttttgg | aatcattgaa | atatgttgaa | 120 |
| gctaacaaag | gtgccatcaa | ccatttgtcc | gatttgtcat | tggatgaatt | caaaaaccgt | 180 |
| tatttgatga | gtgctgaagc | ttttgaacaa | ctcaaaactc | aattcgattt | gaatgccgaa | 240 |
| acaagcgctt | gccgtatcaa | ttcggttaac | gttccatcgg | aattggattt | acgatcactg | 300 |
| cgaactgtca | ctccaatccg | tatgcaagga | ggctgtggtt | catgttgggc | tttctctggt | 360 |
| gtcgccgcaa | ctgaatcagc | ttatttggcc | taccgtaaca | cgtctttgga | tcttctgaa | 420 |
| caggaactcg | tcgattgcgc | atctcaacac | ggatgtcacg | gcgatacaat | accaagaggc | 480 |
| atcgaataca | tccaacaaaa | tggtgtcgtt | gaagaaagaa | gctatccata | cgttgcacga | 540 |
| gaacaacaat | gccgacgacc | aaattcgcaa | cattacggta | tctcaaacta | ctgccaaatt | 600 |
| tatccaccag | atgtgaaaca | aatccgtgaa | gctttgactc | aaacacacac | agctattgcc | 660 |
| gtcattattg | gcattaaaga | tttgagagct | tttcaacatt | atgatggacg | aacaatcatt | 720 |
| caacatgaca | atggttatca | accaaactat | catgccgtca | acattgtcgg | ttacggaagt | 780 |
| acacaaggcg | tcgattattg | gatcgtacga | aacagttggg | atactacctg | gggtgatagc | 840 |

```
ggatacggat atttccaagc cggaaacaac ctcatgatga tcgaacaata tccatatgtt    900
gtaatcatgt ga                                                       912
```

<210> SEQ ID NO 3
<211> LENGTH: 303
<212> TYPE: PRT
<213> ORGANISM: Dermatophagoides farinae

<400> SEQUENCE: 3

```
Arg Pro Ala Ser Ile Lys Thr Phe Glu Glu Phe Lys Lys Ala Phe Asn
1               5                   10                  15

Lys Asn Tyr Ala Thr Val Glu Glu Glu Val Ala Arg Lys Asn Phe
            20                  25                  30

Leu Glu Ser Leu Lys Tyr Val Glu Ala Asn Lys Gly Ala Ile Asn His
        35                  40                  45

Leu Ser Asp Leu Ser Leu Asp Glu Phe Lys Asn Arg Tyr Leu Met Ser
    50                  55                  60

Ala Glu Ala Phe Glu Gln Leu Lys Thr Gln Phe Asp Leu Asn Ala Glu
65                  70                  75                  80

Thr Ser Ala Cys Arg Ile Asn Ser Val Asn Val Pro Ser Glu Leu Asp
                85                  90                  95

Leu Arg Ser Leu Arg Thr Val Thr Pro Ile Arg Met Gln Gly Gly Cys
            100                 105                 110

Gly Ser Cys Trp Ala Phe Ser Gly Val Ala Ala Thr Glu Ser Ala Tyr
        115                 120                 125

Leu Ala Tyr Arg Gln Thr Ser Leu Asp Leu Ser Gln Glu Leu Val
    130                 135                 140

Asp Cys Ala Ser Gln His Gly Cys His Gly Asp Thr Ile Pro Arg Gly
145                 150                 155                 160

Ile Glu Tyr Ile Gln Gln Asn Gly Val Val Glu Glu Arg Ser Tyr Pro
                165                 170                 175

Tyr Val Ala Arg Glu Gln Gln Cys Arg Arg Pro Asn Ser Gln His Tyr
            180                 185                 190

Gly Ile Ser Asn Tyr Cys Gln Ile Tyr Pro Pro Asp Val Lys Gln Ile
        195                 200                 205

Arg Glu Ala Leu Thr Gln Thr His Thr Ala Ile Ala Val Ile Ile Gly
    210                 215                 220

Ile Lys Asp Leu Arg Ala Phe Gln His Tyr Asp Gly Arg Thr Ile Ile
225                 230                 235                 240

Gln His Asp Asn Gly Tyr Gln Pro Asn Tyr His Ala Val Asn Ile Val
                245                 250                 255

Gly Tyr Gly Ser Thr Gln Gly Val Asp Tyr Trp Ile Val Arg Asn Ser
            260                 265                 270

Trp Asp Thr Thr Trp Gly Asp Ser Gly Tyr Gly Tyr Phe Gln Ala Gly
        275                 280                 285

Asn Asn Leu Met Met Ile Glu Gln Tyr Pro Tyr Val Val Ile Met
    290                 295                 300
```

<210> SEQ ID NO 4
<211> LENGTH: 223
<212> TYPE: PRT
<213> ORGANISM: Dermatophagoides farinae

```
<400> SEQUENCE: 4

Thr Ser Ala Cys Arg Ile Asn Ser Val Asn Val Pro Ser Glu Leu Asp
1               5                   10                  15

Leu Arg Ser Leu Arg Thr Val Thr Pro Ile Arg Met Gln Gly Gly Cys
            20                  25                  30

Gly Ser Cys Trp Ala Phe Ser Gly Val Ala Ala Thr Glu Ser Ala Tyr
        35                  40                  45

Leu Ala Tyr Arg Gln Thr Ser Leu Asp Leu Ser Glu Gln Glu Leu Val
    50                  55                  60

Asp Cys Ala Ser Gln His Gly Cys His Gly Asp Thr Ile Pro Arg Gly
65                  70                  75                  80

Ile Glu Tyr Ile Gln Gln Asn Gly Val Val Glu Arg Ser Tyr Pro
                85                  90                  95

Tyr Val Ala Arg Glu Gln Gln Cys Arg Arg Pro Asn Ser Gln His Tyr
            100                 105                 110

Gly Ile Ser Asn Tyr Cys Gln Ile Tyr Pro Pro Asp Val Lys Gln Ile
            115                 120                 125

Arg Glu Ala Leu Thr Gln Thr His Thr Ala Ile Ala Val Ile Ile Gly
        130                 135                 140

Ile Lys Asp Leu Arg Ala Phe Gln His Tyr Asp Gly Arg Thr Ile Ile
145                 150                 155                 160

Gln His Asp Asn Gly Tyr Gln Pro Asn Tyr His Ala Val Asn Ile Val
                165                 170                 175

Gly Tyr Gly Ser Thr Gln Gly Val Asp Tyr Trp Ile Val Arg Asn Ser
            180                 185                 190

Trp Asp Thr Thr Trp Gly Asp Ser Gly Tyr Gly Tyr Phe Gln Ala Gly
        195                 200                 205

Asn Asn Leu Met Met Ile Glu Gln Tyr Pro Tyr Val Val Ile Met
        210                 215                 220

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgtaaaacga cggccagt                                                         18

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caggaaacag ctatgac                                                          17

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 7
ggtattaacg gtttcggacg tattg                                          25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gatgttgaca gggtctctct cttgg                                          25

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gactggttcc aattgacaag c                                              21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggcaaatggc attctgacat                                                20
```